US009346760B2

(12) United States Patent
Biswas et al.

(10) Patent No.: US 9,346,760 B2
(45) Date of Patent: May 24, 2016

(54) PROCESS FOR THE PREPARATION OF (S)-(+)- OR (R)-(-)-10-HYDROXY DIHYDRODIBENZ[B,F]AZEPINES BY ENANTIOSELECTIVE REDUCTION OF 10,11-DIHYDRO-10-OXO-5H-DIBENZ[B,F] AZEPINES AND POLYMORPHS THEREOF

(75) Inventors: Sujay Biswas, Noida (IN); Shailendra Kumar Dubey, Noida (IN); Vikas Bansal, Noida (IN); Mukesh Masand, Noida (IN); Dharam Vir, Noida (IN)

(73) Assignee: JUBILANT LIFE SCIENCES LIMITED, Noida (IN)

( * ) Notice: Subject to any disclaimer, the term of this patent is extended or adjusted under 35 U.S.C. 154(b) by 212 days.

(21) Appl. No.: 14/004,103

(22) PCT Filed: Mar. 6, 2012

(86) PCT No.: PCT/IB2012/000410
§ 371 (c)(1),
(2), (4) Date: Sep. 9, 2013

(87) PCT Pub. No.: WO2012/120356
PCT Pub. Date: Sep. 13, 2012

(65) Prior Publication Data
US 2013/0345198 A1    Dec. 26, 2013

(30) Foreign Application Priority Data

Mar. 8, 2011  (IN) .............................. 638/DEL/2011
Mar. 30, 2011 (IN) .............................. 903/DEL/2011

(51) Int. Cl.
*A61K 31/55*     (2006.01)
*C07D 223/22*    (2006.01)
*C07D 223/28*    (2006.01)

(52) U.S. Cl.
CPC ............ *C07D 223/28* (2013.01); *C07D 223/22* (2013.01); *Y10T 428/2982* (2015.01)

(58) Field of Classification Search
CPC ..... A61K 31/55; C07D 223/22; C07D 223/28
USPC ................... 514/217; 540/589, 591
See application file for complete search history.

(56) References Cited

U.S. PATENT DOCUMENTS

2007/0196488 A1† 8/2007 Kalb et al.

FOREIGN PATENT DOCUMENTS

| WO | 02092572 | A1 † | 11/2002 |
| WO | 2004/031155 | A1 | 4/2004 |
| WO | 2006005951 | A1 † | 1/2006 |
| WO | 2007012793 | A1 † | 2/2007 |
| WO | 2010113179 | A2 † | 10/2010 |
| WO | 2011/091131 | A2 | 7/2011 |
| WO | 2011/138795 | A2 | 11/2011 |

OTHER PUBLICATIONS

J. Benes et al., Anticonvulsant and sodium channel-blocking properties of novel 10,11-dihydro-5H-dibenz[b,f] azepine-5-carboxamide derivatives J Med Chem. Jul. 15, 1999;42(14):2582-7.
J. Suri et al., "Enantioselective reduction of aryl ketones using LiBH4 and TarB-X: a chiral Lewis acid" Tetrahedron Letters, vol. 43, Issue 20, May 13, 2002, pp. 3649-3652.
G. Boullay; Enhancing the Dissolution of Active Principles Why? How? Dec. 5, 1984; Faculte de Pharmacie de Paris-Sud.†
Rudolf Voiogt; Section Improvement of Solubility; 1987; Berlin.†
R.R. Levine; Pharmacology; Drug Actions and Reactions, 1985.†
K. Mingard et al.; Good Practice Guide for Improving the Consistency of Particle Size Measurement; Department for Innovation, Universities & Skills; National Physical Laboratory, 2009.†
Brian S. Furniss, et al.; Textbook of Practical Organic Chemistry, 1996.†
Harry G. Brittain; Polymorphism in Pharmaceuticak Solids; 2009; Drugs and the Pharmaceutical Sciences.†

† cited by third party

*Primary Examiner* — Brenda Coleman
(74) *Attorney, Agent, or Firm* — Maschoff Brennan

(57) ABSTRACT

The present invention provides a novel process for the preparation of substituted optically pure (S)-(+)- or (R)-(−)-10-hydroxy-dihydrodibenz[b,f]azepines or derivatives thereof, starting from 10,11-dihydro-10-oxo-5H-dibenz[b,f]azepines using boronate esters or their derivatives. The present invention also provides use of thus prepared (S)-(+)- or (R)-(−)-10-hydroxy-dihydrodibenz[b,f]azepines for the preparation of their ester such as (S)-(−)-10-acetoxy-10,11-dihydro-5H-dibenz[b,f]azepine-5-carboxamide or (R)-(+)-10-acetoxy-10,11-dihydro-5H-dibenz[b,f]azepine-5-carboxamide. The present invention also provides novel solid state crystalline forms $J_1$, $J_2$, $J_3$, $J_4$ and amorphous form of eslicarbazepine and the process for the preparation thereof. Also, the present invention provides novel solid state crystalline form and amorphous form of eslicarbazepine acetate and the process for the preparation thereof. The novel solid state forms of eslicarbazepine are useful for the preparation of derivatives of eslicarbazepine such as eslicarbazepine acetate.

14 Claims, 14 Drawing Sheets

TGA

PROCESS FOR THE PREPARATION OF (S)-(+)- OR (R)-(−)-10-HYDROXY DIHYDRODIBENZ[B,F]AZEPINES BY ENANTIOSELECTIVE REDUCTION OF 10,11-DIHYDRO-10-OXO-5H-DIBENZ[B,F] AZEPINES AND POLYMORPHS THEREOF

FIELD OF THE INVENTION

The present invention relates to a novel process for the preparation of substituted optically pure (S)-(+)- or (R)-(−)-10-hydroxy-dihydrodibenz[b,f]azepines or derivatives thereof, starting from 10,11-dihydro-10-oxo-5H-dibenz[b,f] azepines using boronate esters or their derivatives. More particularly, the present invention provides a novel process for the preparation of (S)-(+)- or (R)-(−)-10,11-dihydro-10-hydroxy-5H-dibenz[b,f]azepine-5-carboxamide by enantioselective reduction of 10,11-dihydro-10-oxo-5H-dibenz[b,f] azepine-5-carboxamide using boronate esters or their derivatives. The present invention also provides use of thus prepared (S)-(+)- or (R)-(−)-10-hydroxy-dihydrodibenz[b,f] azepines for the preparation of their ester such as (S)-(−)-10-acetoxy-10,11-dihydro-5H-dibenz[b,f]azepine-5-carboxamide, or (R)-(+)-10-acetoxy-10,11-dihydro-5H-dibenz[b,f] azepine-5-carboxamide.

Further, the present invention also provides novel solid state forms of eslicarbazepine and process for the preparation thereof. Further, it relates to the pharmaceutical composition and method of using the formulation to treat conditions in a subject in need thereof. The solid state forms of eslicarbazepine are useful for the treatment of psychosomatic disturbances, epilepsy, trigeminal neuralgia, cerebral spasticity, affective brain disorder or nervous function alteration in degenerative and post-ischemic disease, bipolar disorder and the like. Also, the novel solid state forms of eslicarbazepine are useful for the preparation of derivatives of eslicarbazepine such as eslicarbazepine acetate.

BACKGROUND OF THE INVENTION

Racemic(±)-10,11-dihydro-10-hydroxy-5H-dibenz[b,f] azepine-5-carboxamide (licarbazepine) is the principal metabolite of the established anti-epileptic drug oxcarbazepine. This compound has been shown to possess valuable pharmacological properties and a particularly high therapeutic index. In the case of oral or rectal administration it has a central depressant action, an anticonvulsive action, which relaxes the central muscular system and inhibits the fighting reaction of the mouse. These properties determined by selected standard tests [R. Domenjoz and W. Theobald, *Arch. Int. Pharmacodyn.* 120, 450 (1959) and W. Theobald et al., *Arzneimittel Forsch.* 17, 561 (1967)] characterize the compound as being suitable for the treatment of psychosomatic disturbances, epilepsy, trigeminal neuralgia and cerebral spasticity.

Eslicarbazepine acetate is a prodrug of eslicarbazepine (S-licarbazepine), a third-generation drug belonging to the carbamazepine family and the active metabolite of oxcarbazepine. (S)-(+)-10,11-Dihydro-10-hydroxy-5H-dibenz[b,f] azepine-5-carboxamide (eslicarbazepine) is the key intermediate for the synthesis of antiepilectic drug substance eslicarbazepine acetate.

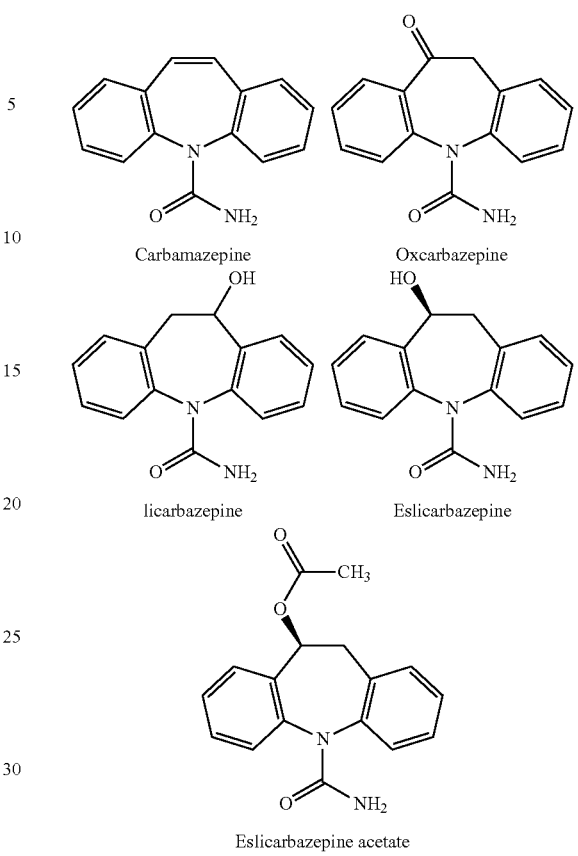

The synthesis and improved anticonvulsant properties of (S)-(−)-10-acetoxy-10,11-dihydro-5H-dibenz[b,f]azepine-5-carboxamide (BIA 2-093), and (R)-(+)-10-acetoxy-10,11-dihydro-5H-dibenz[b,f]azepine-5-carboxamide (BIA 2-059) have been described by Benes, J. et al., in U.S. Pat. No. 5,753,646 and *J. Med. Chem.*, 42, 2582-2587 (1999). The key step of the synthesis of compounds BIA 2-093 and BIA 2-059 involves the resolution of racemic 10,11-dihydro-10-hydroxy-5H-dibenz[b,f]azepine-5-carboxamide into its separate, optically pure enantiomers, (S)-(+)-10,11-dihydro-10-hydroxy-5H-dibenz[b,f]azepine-5-carboxamide and (R)-(−)-10,11-dihydro-10-hydroxy-5H-dibenz[b,f]azepine-5-carboxamide by esterification of racemic 10,11-dihydro-10-hydroxy-5H-dibenz[b,f]azepine-5-carboxyamide with menthoxyacetic acid, separation of the resulting diasteroisomers followed by hydrolysis of the respective optically active menthoxyacetates leads to optically pure enantiomers.

One of the disadvantages of this method is that it can only be utilized for the preparation of only small quantities of each stereoisomer because the necessary optically pure resolving agents, (+) and (−)-menthoxyacetic acid are enormously expensive and are not readily available in sufficient quantities from commercial sources.

U.S. Pat. No. 7,119,197 discloses a method for the preparation of optically pure (S)-(+)-10,11-dihydro-10-hydroxy-5H-dibenz[b,f]azepine-5-carboxamide and (R)-(−)-10,11-dihydro-10-hydroxy-5H-dibenz[b,f]azepine-5-carboxamide by resolution of racemic (±)-10,11-dihydro-10-hydroxy-5H-dibenz[b,f]azepine-5-carboxamide using an appropriate tartaric acid anhydride.

US2006142566 discloses a method for the enantioselective preparation of the (S) and (R)-enantiomers of 10,11-dihydro-10-hydroxy-5H-dibenz[b,f]azepine-5-carboxamide by asymmetric reduction of oxcarbazepine. The asymmetric reduction is carried out in the presence of a ruthenium catalyst and a hydride source. A suitable catalyst may be formed from [RuCl₂(p-cymene)]₂ and (S,S) or (R,R)—N-(4-toluenesulfonyl)-diphenylethylenediamine. US 2006/0142566 also discloses two crystalline Forms A and B of both the enantiomers of 10,11-dihydro-10 hydroxy-5Hdibenz[b,f]azepine-5-carboxamide, obtainable by the new processes and their usage in the production of pharmaceutical preparations.

US2009203902 discloses a process for preparing (S)-(+)- or (R)-(−)-10,11-dihydro-10-hydroxy-5H-dibenz[b,f]azepine-5-carboxamide, by reduction of oxcarbazepine in the presence of a catalyst and a hydride source. The catalyst is prepared from a combination of [RuX₂(L)]₂ wherein X is chlorine, bromine or iodine, and L is an aryl or aryl-aliphatic ligand with a ligand of following formula, wherein the variables are as defined in US2009203902. The disadvantage of this process is again the use of ruthenium complex as a catalyst.

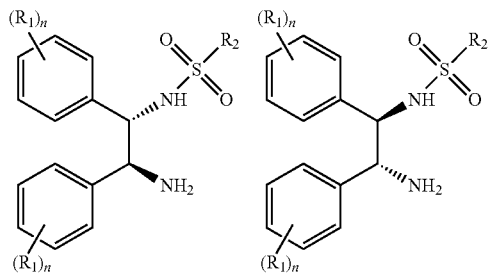

US 2010173893 discloses a process for preparing eslicarbazepine acetate ((S)-(−)-10-acetoxy-10,11-dihydro-5H-dibenz[b,f]azepine-5-carboxamide) and R-(+)-licarbazepine acetate ((R)-(+)-10-acetoxy-10,11-dihydro-5H-dibenz[b,f]azepine-5-carboxamide) and their derivatives by asymmetric hydrogenation of the corresponding enol acetate or of the corresponding enol ester derivative using a chiral catalyst and a source of hydrogen. The chiral catalyst is selected from Rh(I) complexes having chiral ligands with the following structures.

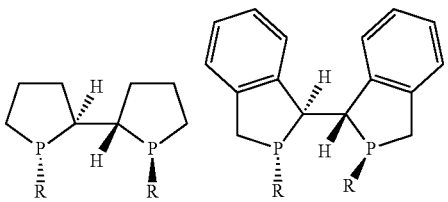

The major disadvantages of the above mentioned processes is the residual level of ruthenium/rhodium metal, a most undesirable contaminant in the product, which is high and difficult to remove in a dosage form for the human consumption. Furthermore, these catalysts are expensive and therefore their use can not be regarded as industrially viable.

US 2009105472 discloses a process for preparing (S)-(+)-10,11-dihydro-10-hydroxy-5H-dibenz[b,f]azepine-5-carboxamide starting from racemic 5-cyano-10,11-dihydro-10-hydroxy-5H-dibenz[b,f]azepine by (a) phthaloylation, (b) treating with chiral amine (c) separation of the diastereomeric salts of the phthaloyl derivative with (S)-phenylethylamine, (d) generation of half ester followed by hydrolysis to (S)-(+)-5-cyano-10,11-dihydro-10-hydroxy-5H-dibenz[b,f]azepine and (e) hydrolysis of the nitrile group of the latter to amido group, by treatment with peroxy compounds in alkali medium (Scheme I).

Scheme I

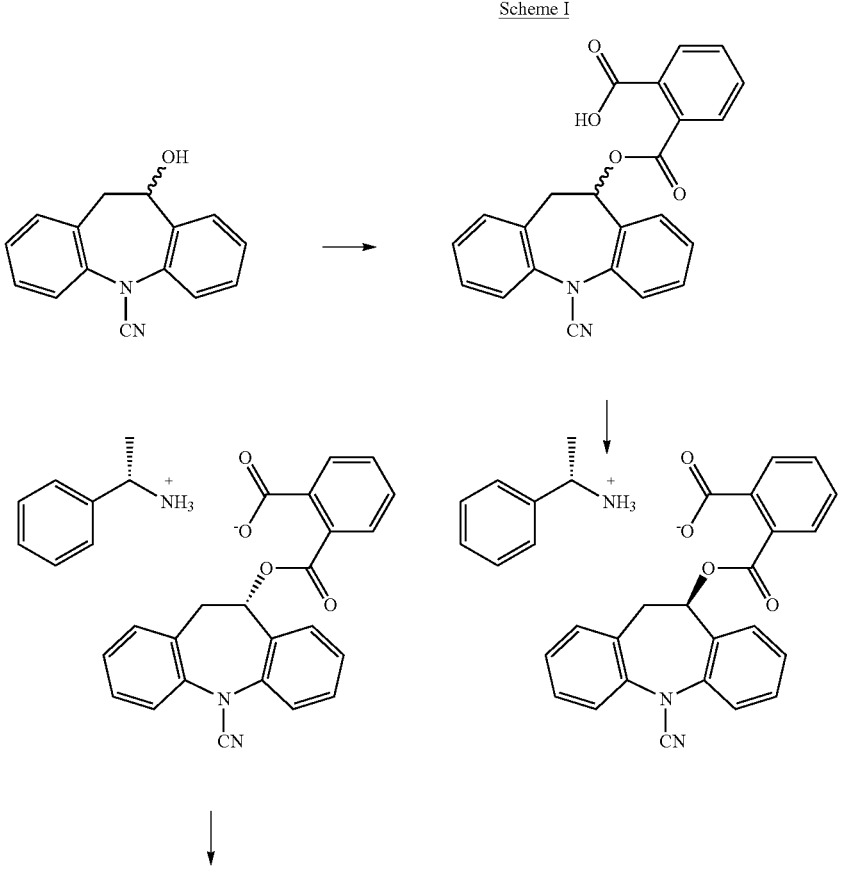

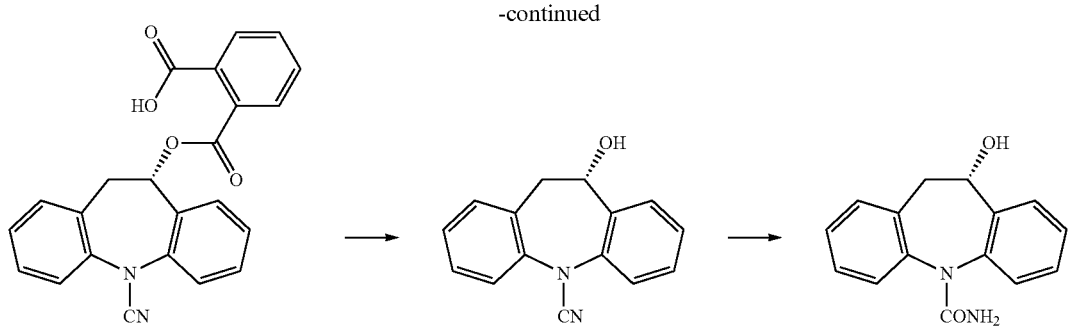

Accordingly, for obtaining the optically pure compound, the five steps sequence is carried out, involving more numbers of reagents and solvents, while increasing the time cycle of the entire sequence. Thus, there remains a need for an environment friendly, industrially feasible and economical process for the preparation of (S)-(+)- and (R)-(−)-10-hydroxy-dihydrodibenz[b,f]azepines.

Therefore, a process is required, which avoids expensive menthoxyacetic acid, used in the known process for the preparation of (S)-(+)- and (R)-(−)-10-hydroxy-dihydro dibenz[b,f]azepines. Moreover, a process is required, which does not involve the use of any transition metal (e.g. ruthenium or rhodium catalyst), the most undesirable contaminant in the product, for asymmetric catalytic reduction of corresponding keto analogue. Furthermore, the transition metals (e.g. ruthenium or rhodium catalyst) are expensive and therefore their use can not be regarded as industrially viable.

*Pharmaceutical Research*, (2008), 25, 530, explains that the ability to deliver the drug to the patient in a safe, efficacious and cost effective way depends largely upon the physicochemical properties of the APIs in the solid state and accordingly one of the challenging tasks in the pharmaceutical industry is to design pharmaceutical materials with specific physiochemical properties. It is known that different solid forms of the same drug may exhibit different properties, including characteristics that have functional implications with respect to their use as drug may have substantial differences in such pharmaceutically important properties as dissolution rates and bioavailability. Likewise, different polymorphs may have different processing properties, such as hygroscopisity, flow ability and the like, which could affect their suitability as active pharmaceuticals for commercial production. Also, it is known in the art that the amorphous forms of APIs generally exhibit the better solubility profile over the corresponding crystalline forms. This is because the lattice energy does not have to be overcome in order to dissolve the solid state structure as in the case for crystalline forms.

Thus, there is a need to develop the novel solid state forms of pharmaceutically active compound, having better physicochemical properties; specially, for the enhancement of the solubility. Also, there is a constant need to have the cost effective and industrial friendly process for the preparation of the solid state form.

DESCRIPTION OF THE INVENTION

Figure 1:
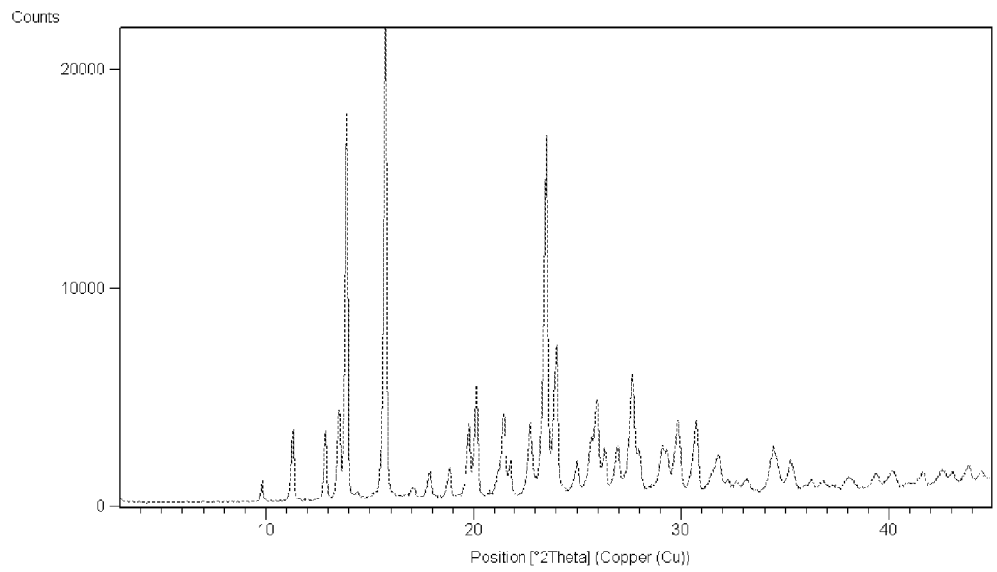
FIG. 1 is a characteristic X-ray powder diffraction ("XRPD") pattern of polymorphic Form $J_1$ of eslicarbazepine.
Figure 2:
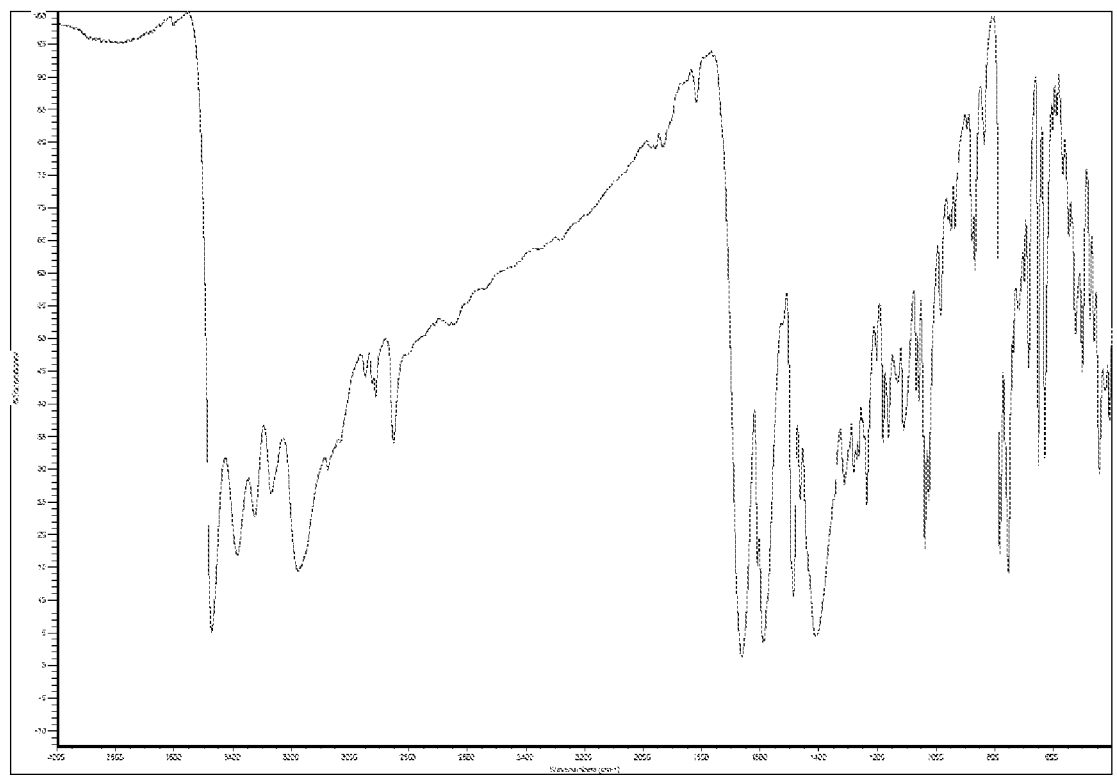
FIG. 2 is a characteristic infra red (IR) spectrum of polymorphic Form $J_1$ of eslicarbazepine.
Figure 3:
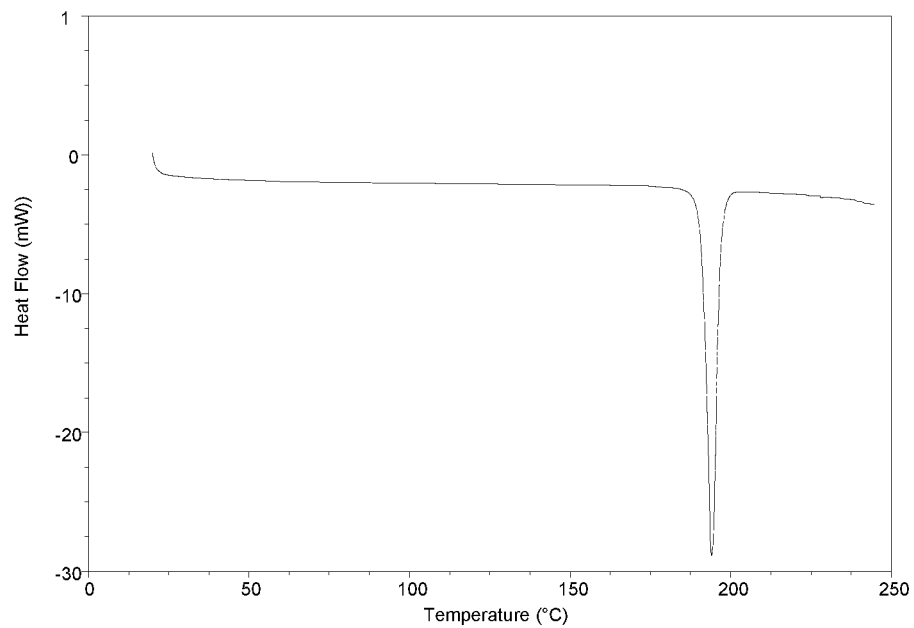
FIG. 3 is a characteristic Differential Scanning calorimetry (DSC) thermogram of polymorphic Form $J_1$ of eslicarbazepine.
Figure 4:
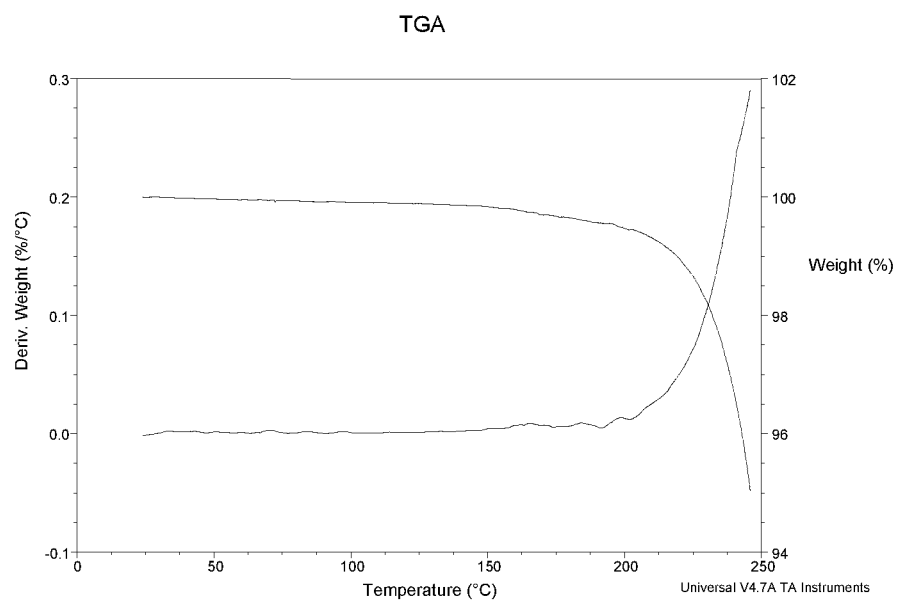
FIG. 4 illustrates the graphic results of a thermogravimetric analysis (TGA) of polymorphic Form $J_1$ of eslicarbazepine.
Figure 5:
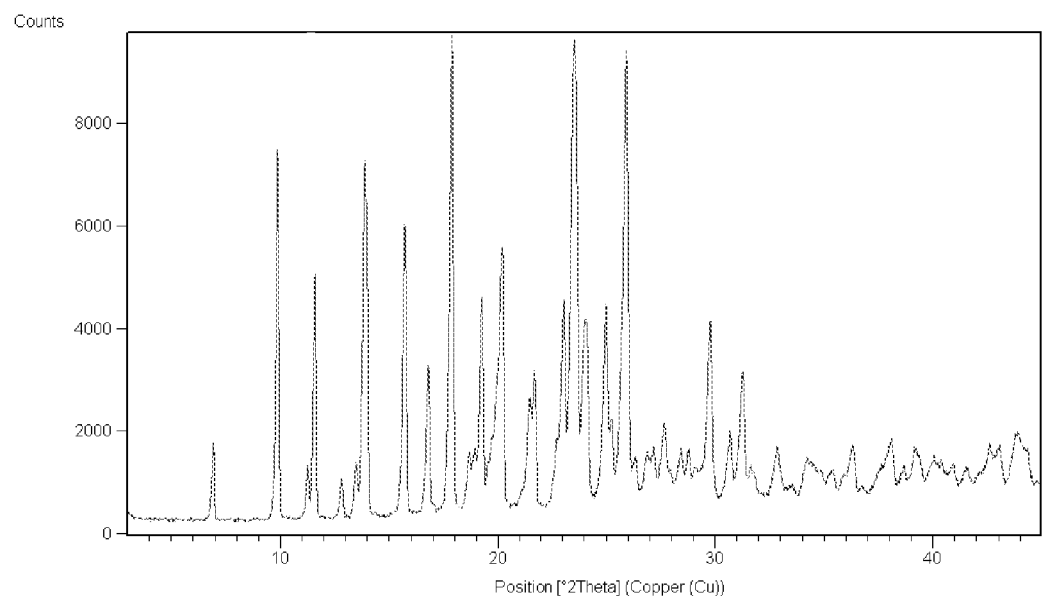
FIG. 5 is a characteristic X-ray powder diffraction ("XRPD") pattern of polymorphic Form $J_2$ of eslicarbazepine.
Figure 6:
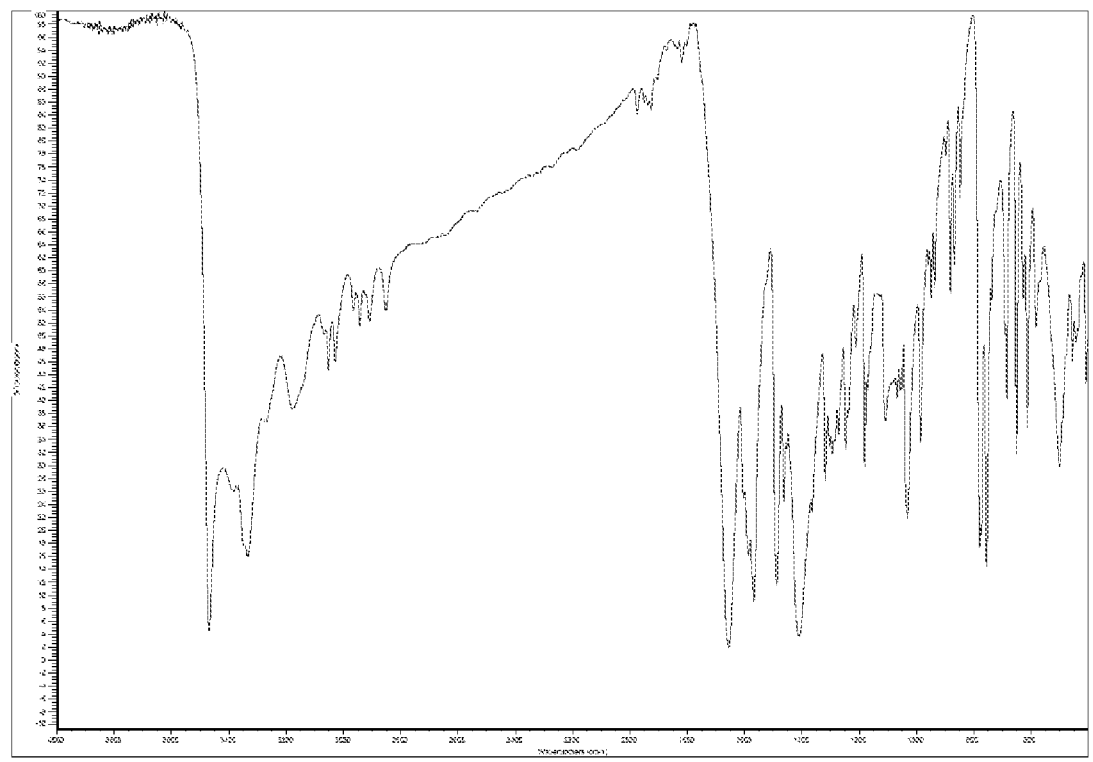
FIG. 6 is a characteristic infra red (IR) spectrum of polymorphic Form $J_2$ of eslicarbazepine.
Figure 7:
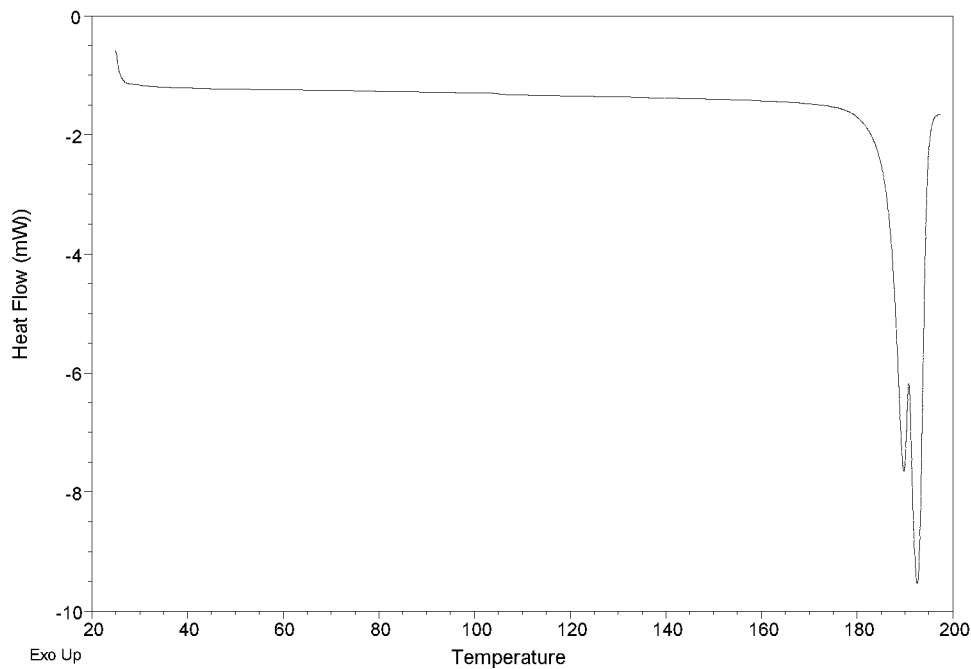
FIG. 7 is a characteristic Differential Scanning calorimetry (DSC) thermogram of polymorphic Form $J_2$ of eslicarbazepine.
Figure 8:
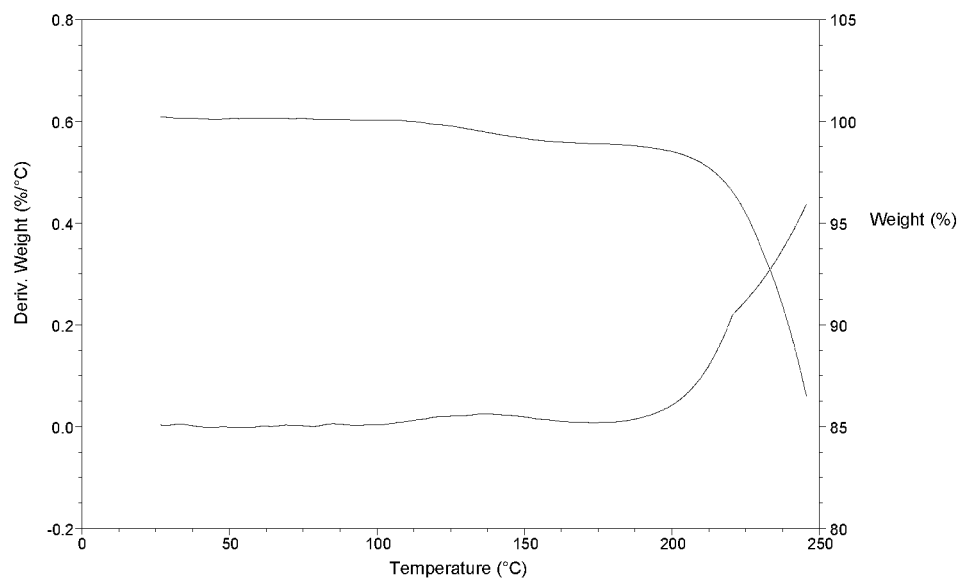
FIG. 8 illustrates the graphic results of a thermogravimetric analysis (TGA) of polymorphic Form $J_2$ of eslicarbazepine.
Figure 9:
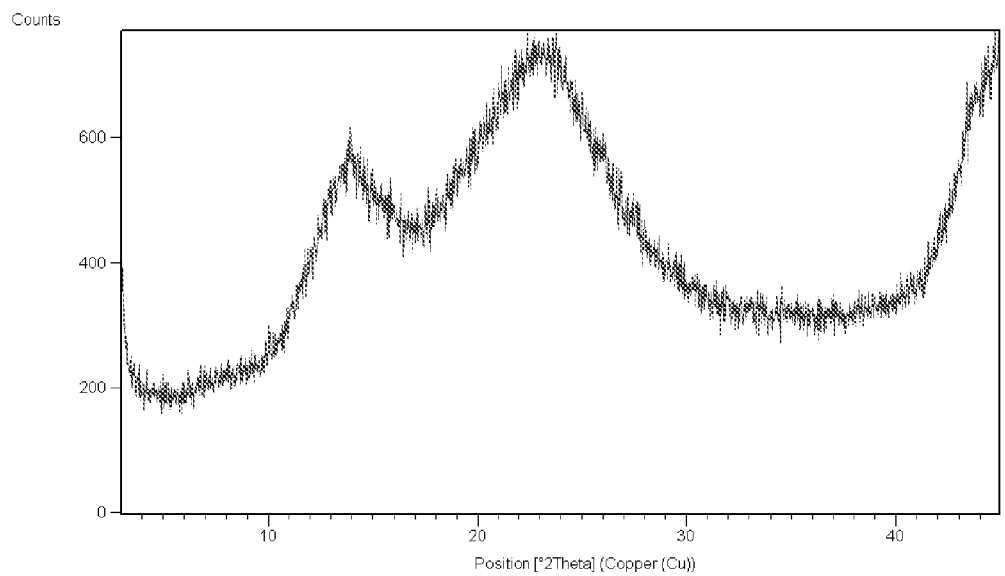
FIG. 9 is a characteristic X-ray powder diffraction ("XRPD") pattern of amorphous eslicarbazepine.
Figure 10:
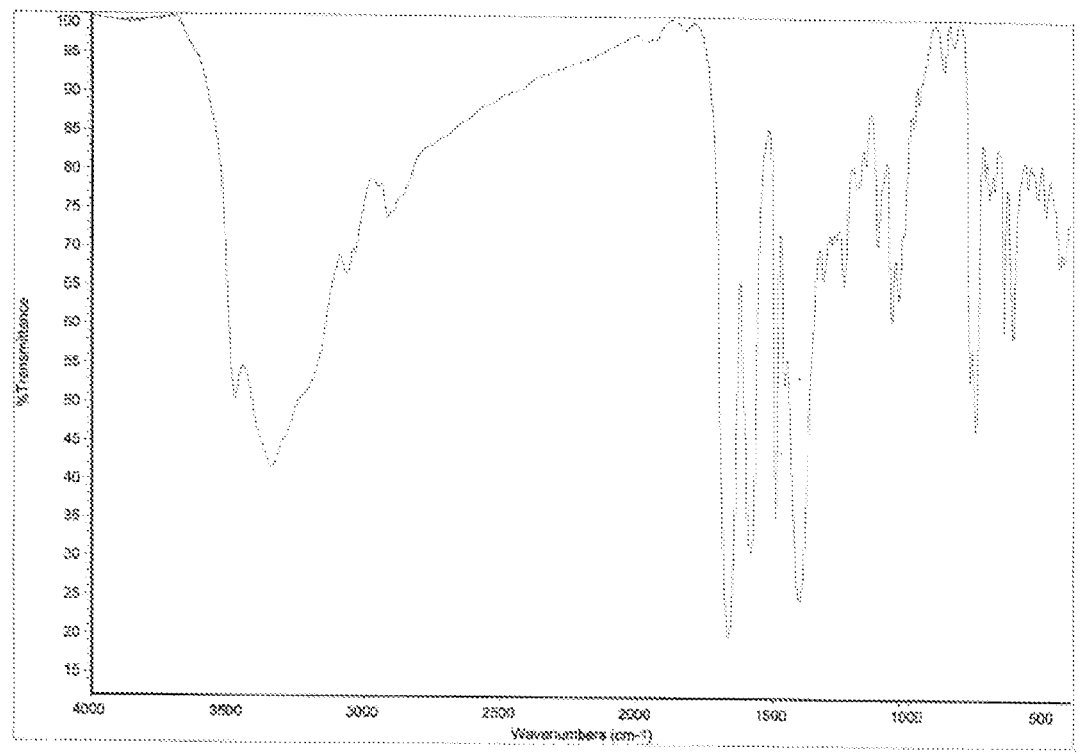
FIG. 10 is a characteristic infra red (IR) spectrum of amorphous eslicarbazepine.
Figure 11:
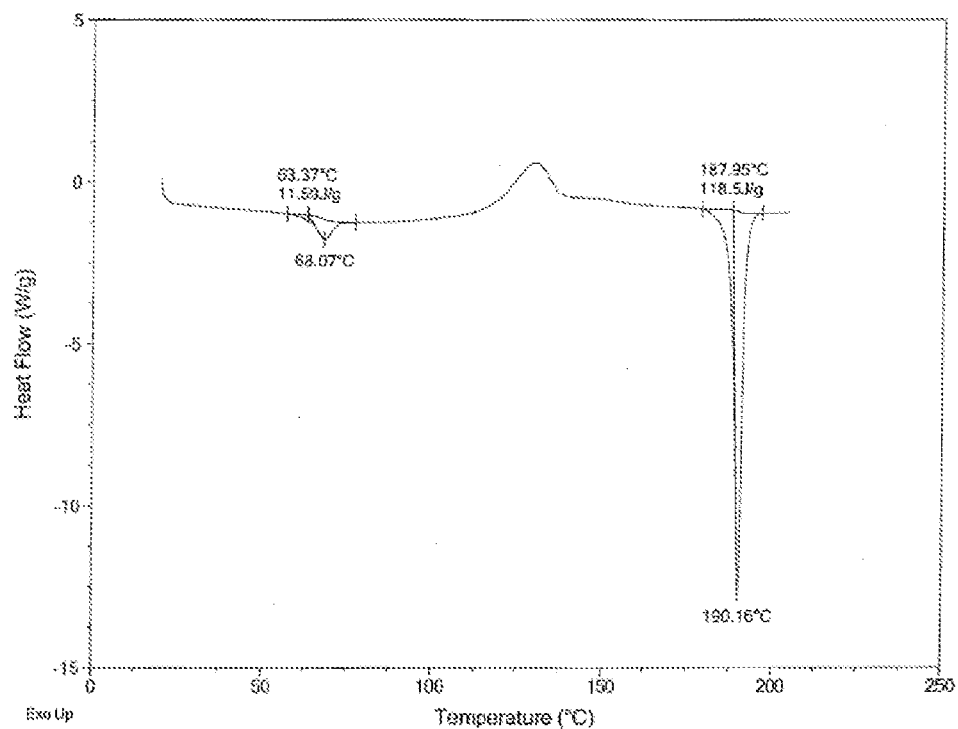
FIG. 11 is a characteristic Differential Scanning calorimetry (DSC) thermogram of amorphous eslicarbazepine.
Figure 12:
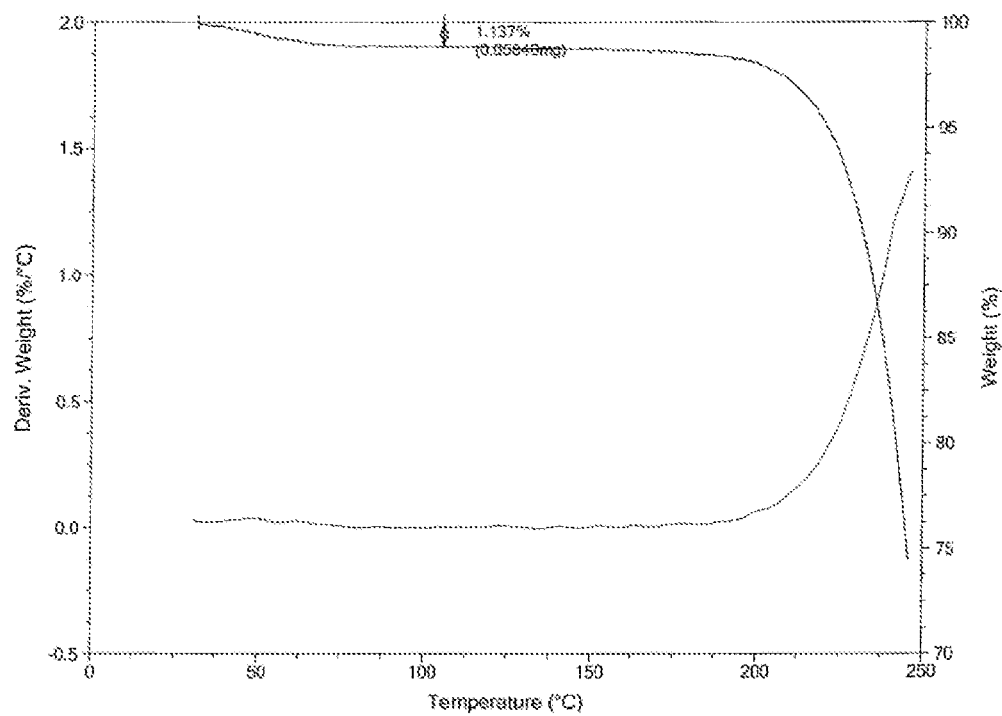
FIG. 12 illustrates the graphic results of a thermogravimetric analysis (TGA) of amorphous eslicarbazepine.
Figure 13:
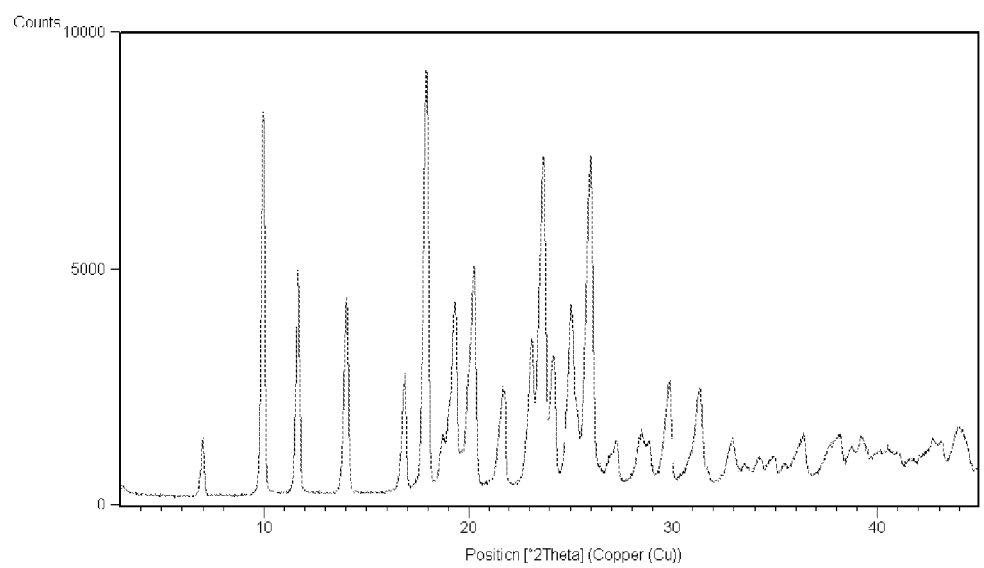
FIG. 13 is a characteristic X-ray powder diffraction ("XRPD") pattern of polymorphic Form $J_3$ of eslicarbazepine.
Figure 14:
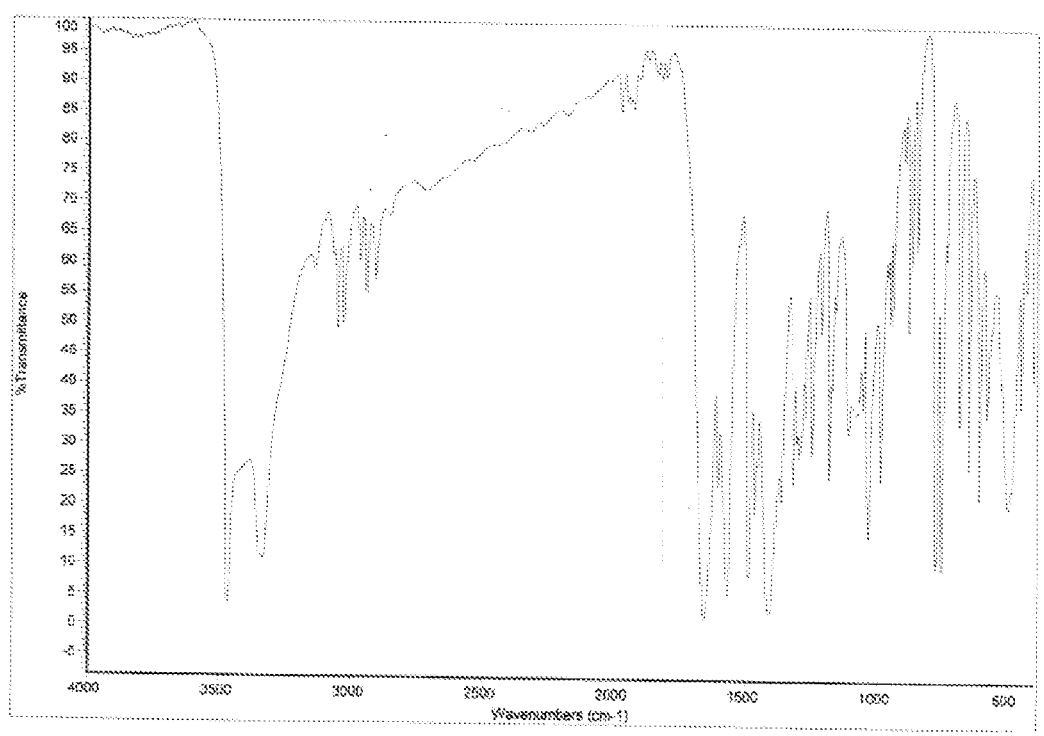
FIG. 14 is a characteristic infra red (IR) spectrum of polymorphic Form $J_3$ of eslicarbazepine.
Figure 15:
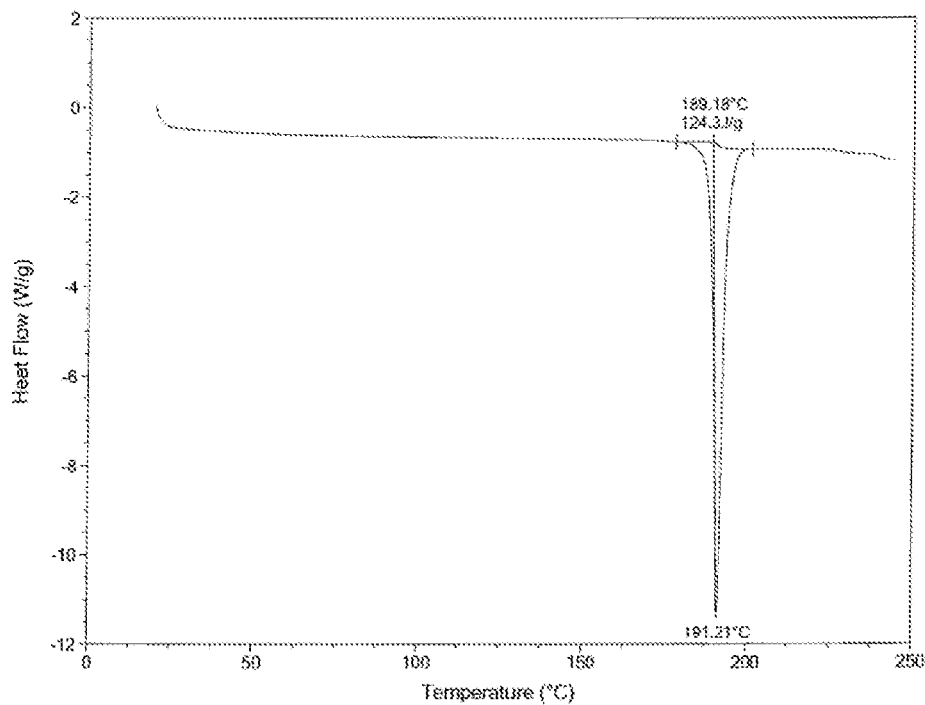
FIG. 15 is a characteristic Differential Scanning calorimetry (DSC) thermogram of polymorphic Form $J_3$ of eslicarbazepine.
Figure 16:
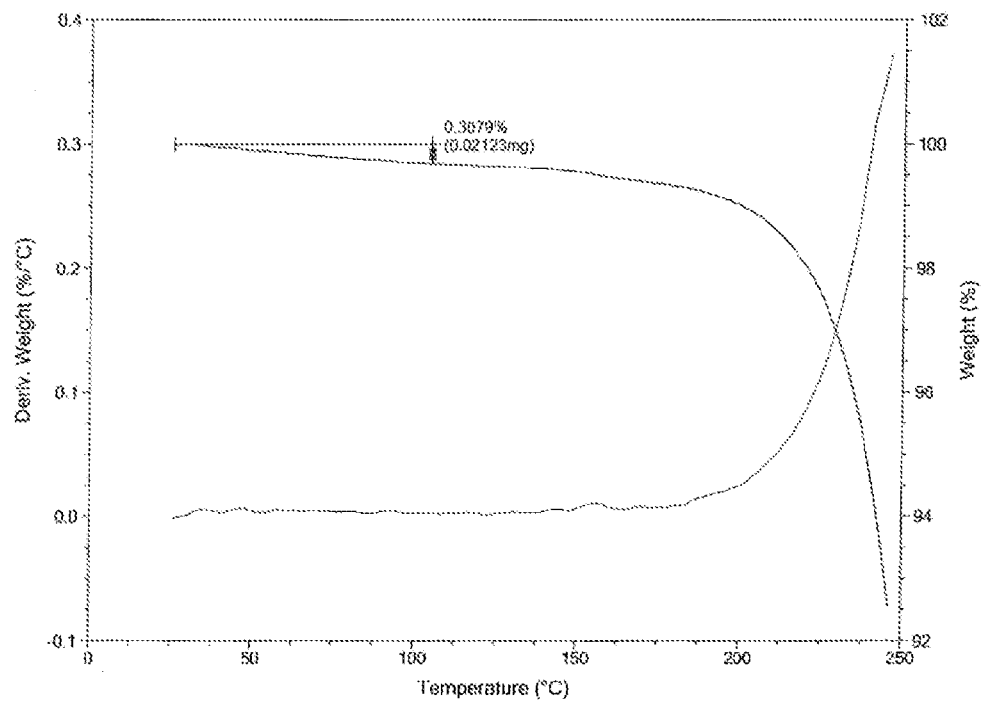
FIG. 16 illustrates the graphic results of a thermogravimetric analysis (TGA) of polymorphic Form $J_3$ of eslicarbazepine.
Figure 17:
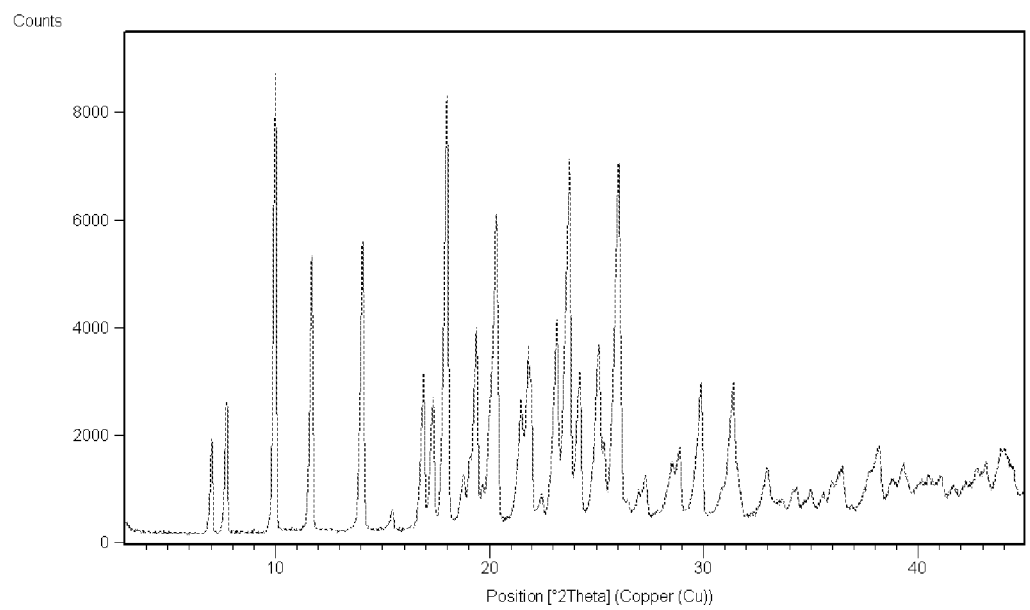
FIG. 17 is a characteristic X-ray powder diffraction ("XRPD") pattern of polymorphic Form $J_4$ eslicarbazepine.
Figure 18:
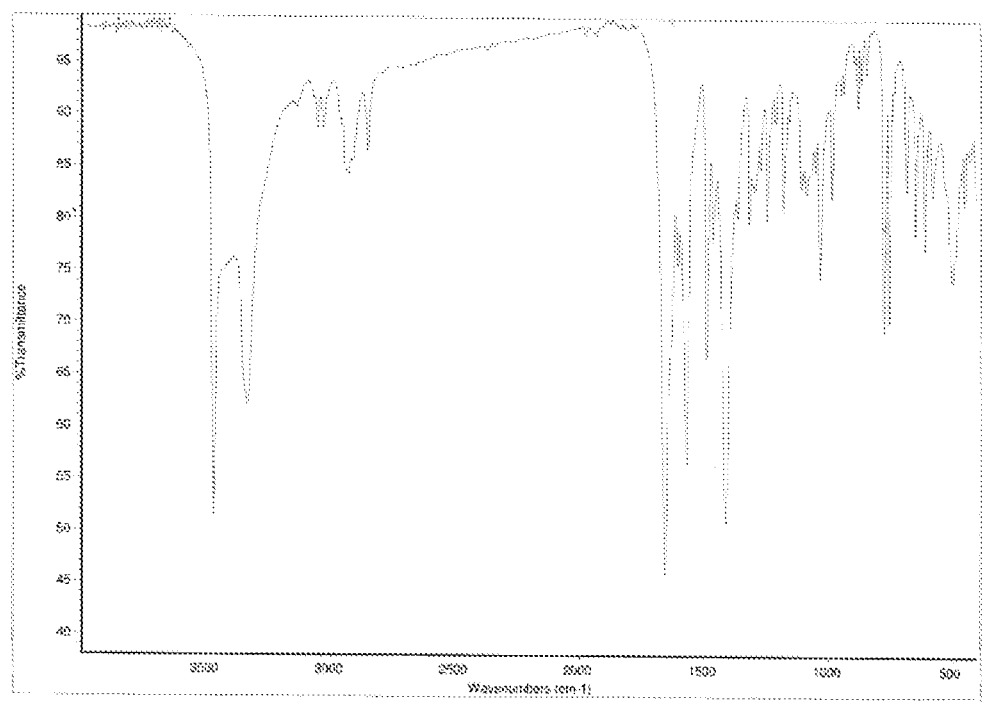
FIG. 18 is a characteristic infra red (IR) spectrum of polymorphic Form $J_4$ eslicarbazepine.
Figure 19:
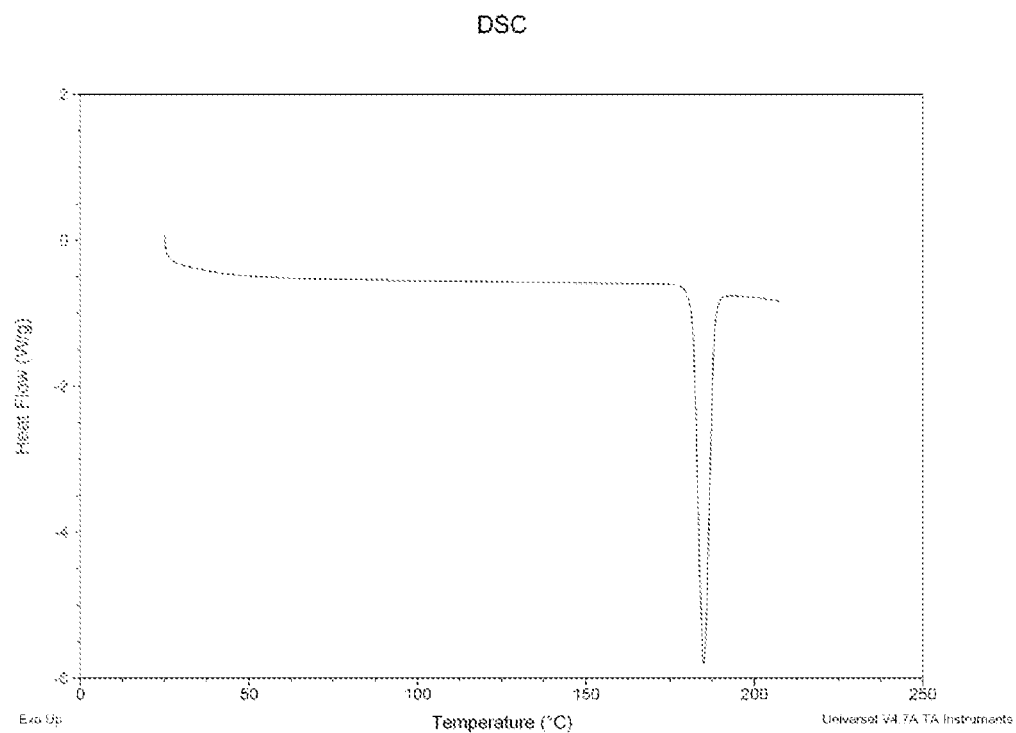
FIG. 19 is a characteristic Differential Scanning calorimetry (DSC) thermogram of polymorphic Form $J_4$ eslicarbazepine.
Figure 20:
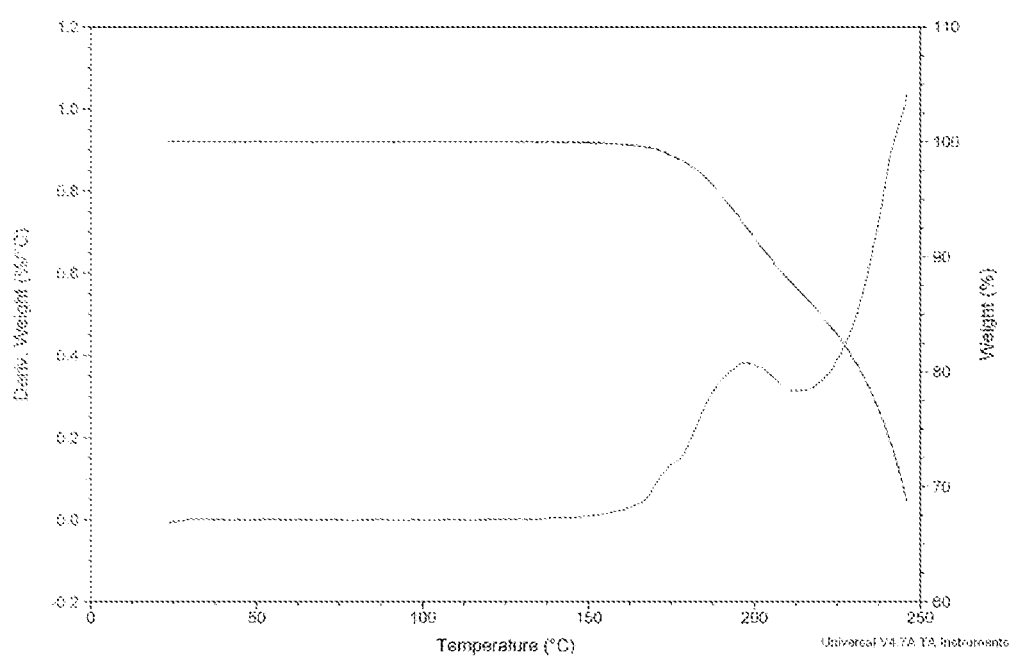
FIG. 20 illustrates the graphic results of a thermogravimetric analysis (TGA) of polymorphic Form $J_4$ eslicarbazepine.
Figure 21:
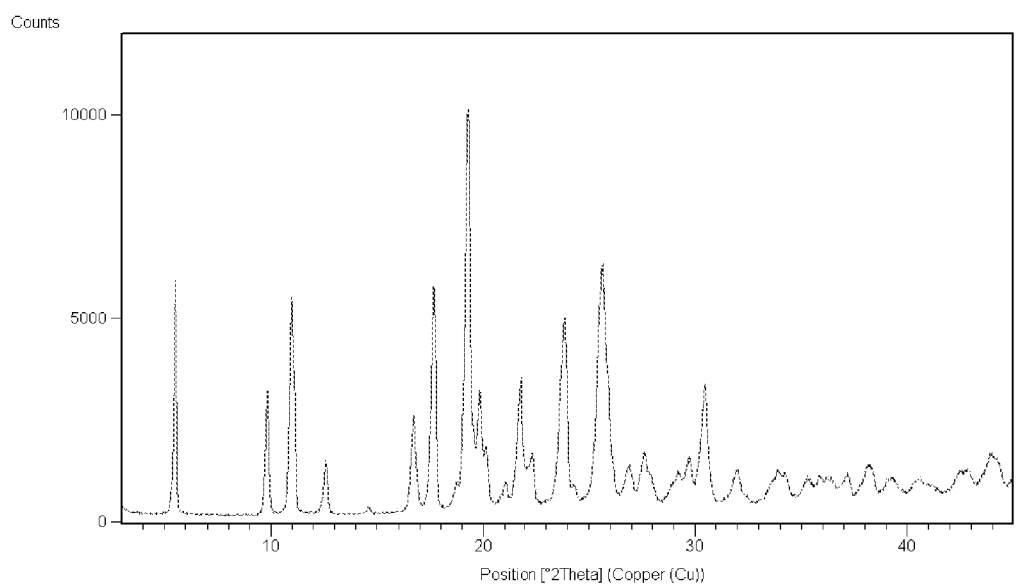
FIG. 21 is a characteristic X-ray powder diffraction ("XRPD") pattern of crystalline Form of eslicarbazepine acetate.
Figure 22:
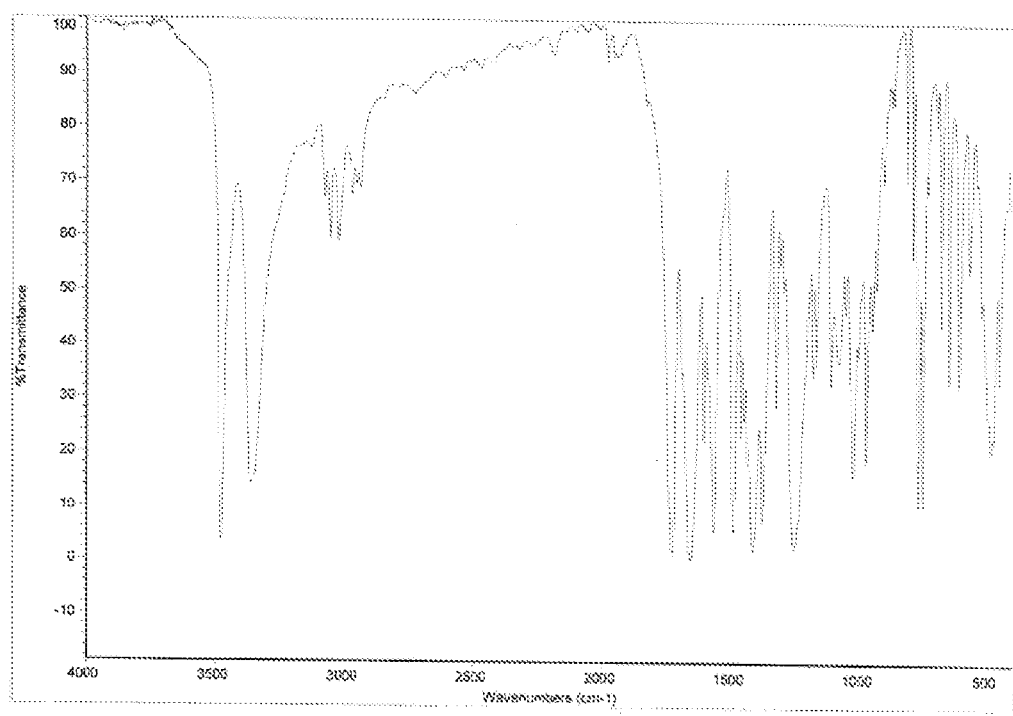
FIG. 22 is a characteristic infra red (IR) spectrum of crystalline Form of eslicarbazepine acetate.
Figure 23:
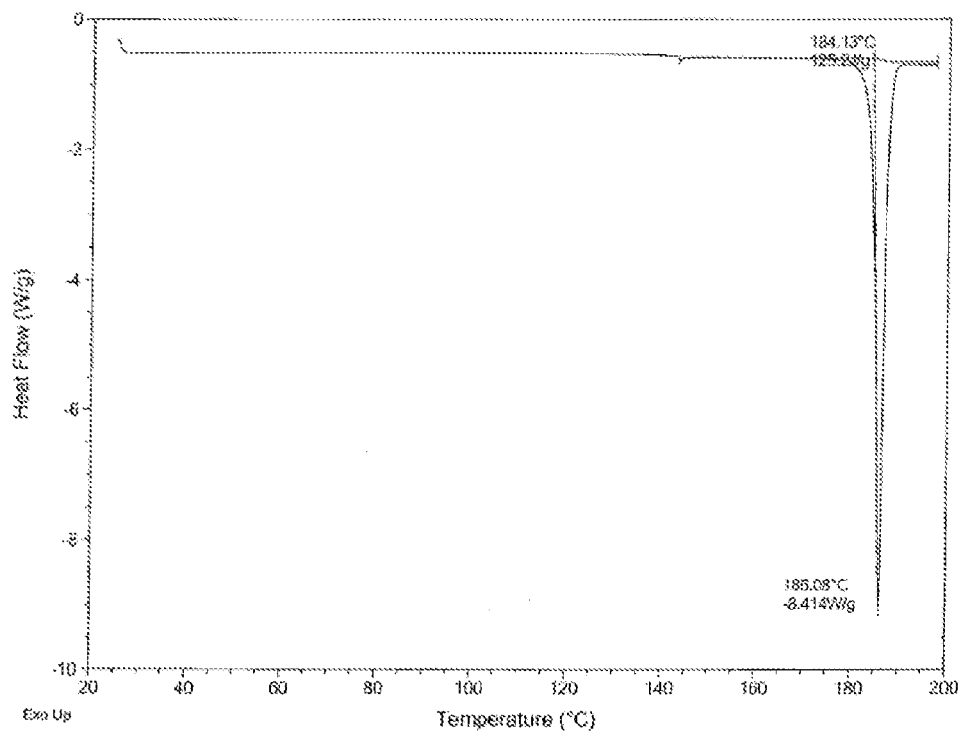
FIG. 23 is a characteristic Differential Scanning calorimetry (DSC) thermogram of crystalline Form of eslicarbazepine acetate.
Figure 24:
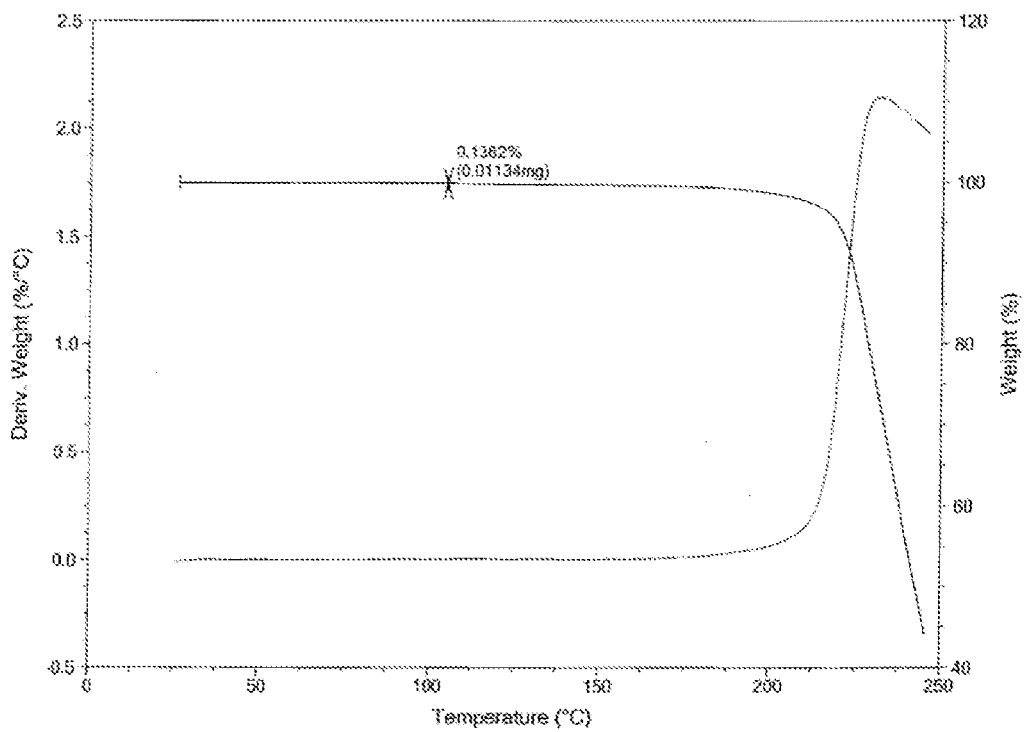
FIG. 24 illustrates the graphic results of a thermogravimetric analysis (TGA) of crystalline Form of eslicarbazepine acetate.
Figure 25:
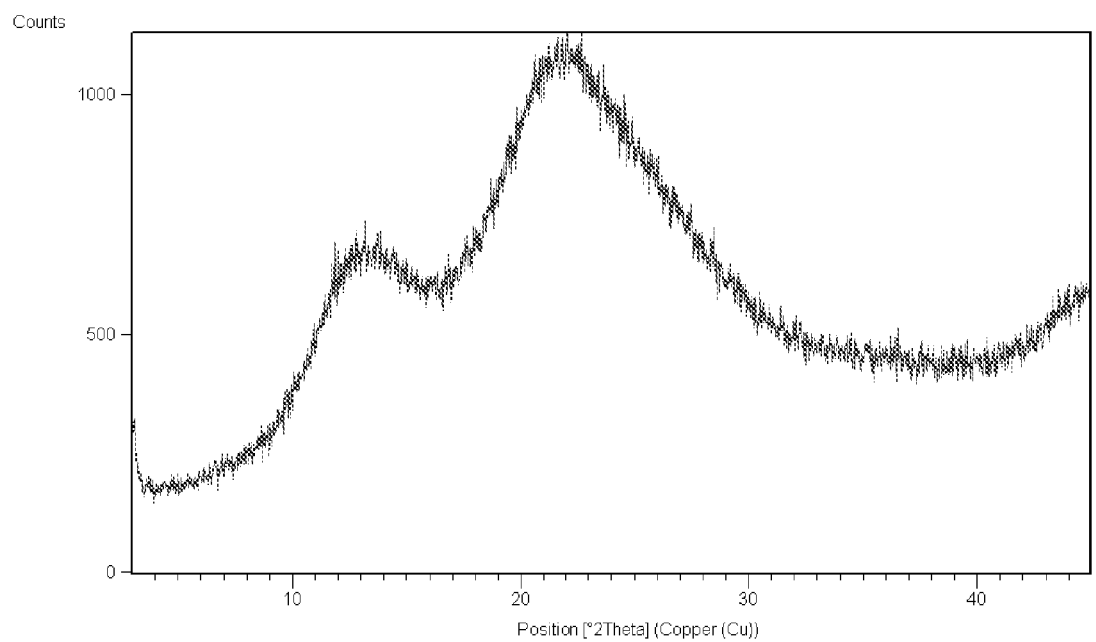
FIG. 25 is a characteristic X-ray powder diffraction ("XRPD") pattern of amorphous Form of eslicarbazepine acetate.
Figure 26:
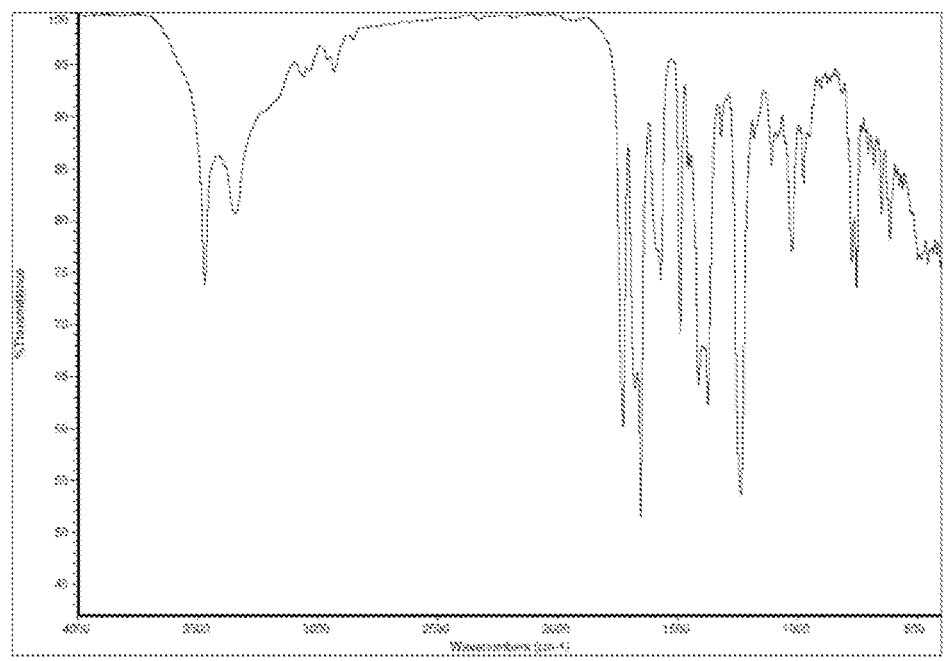
FIG. 26 is a characteristic infra red (IR) spectrum of amorphous Form of eslicarbazepine acetate.
Figure 27:
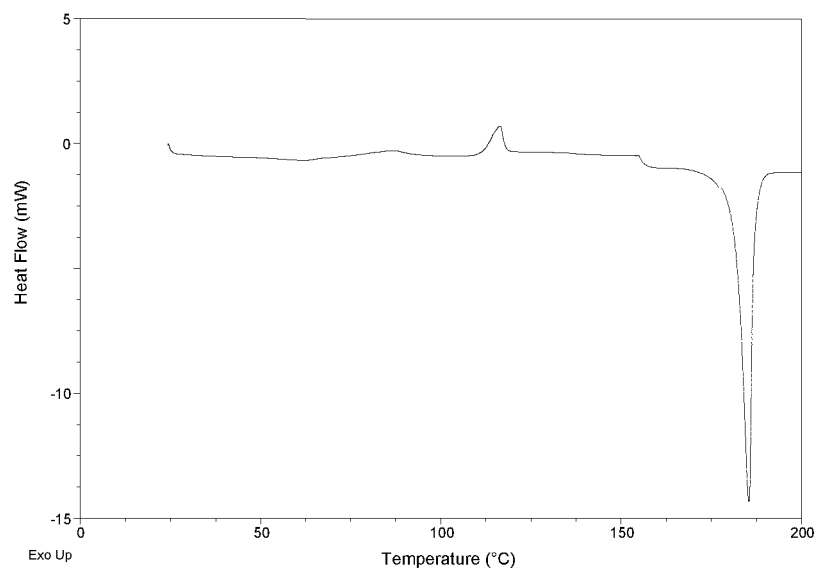
FIG. 27 is a characteristic Differential Scanning calorimetry (DSC) thermogram of amorphous Form of eslicarbazepine acetate.
Figure 28:
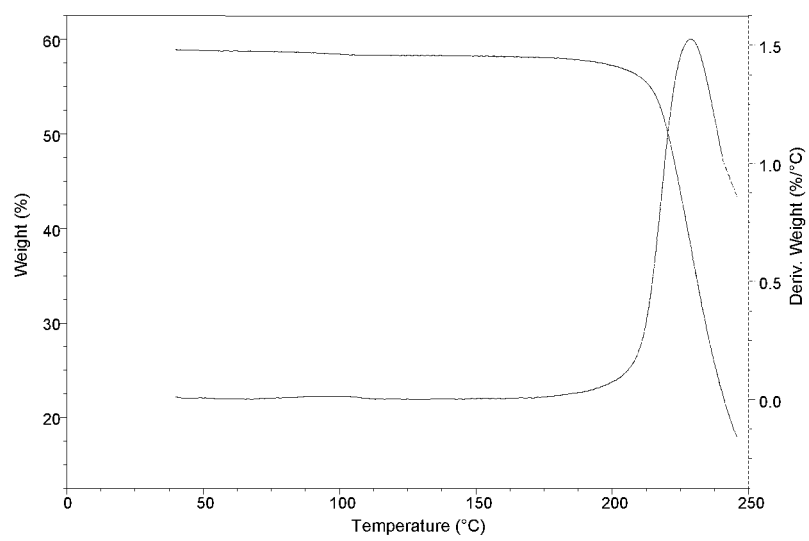
FIG. 28 illustrates the graphic results of a thermogravimetric analysis (TGA) of amorphous Form of eslicarbazepine acetate.

The process of the present invention affords the important advantage of making use of boronate esters, for enantioselective reduction of 10,11-dihydro-10-oxo-5H-dibenz[b,f] azepines (II), which are less expensive and does not lead to undesirable contaminant(s) in the product and does not require any special equipment.

Accordingly, one embodiment of the invention is to provide a method for the preparation of substituted/unsubstituted optically pure (S)-(+)- or (R)-(−)-10-hydroxy-dihydrodibenz [b,f]azepines or derivatives thereof, starting from 10,11-dihydro-10-oxo-5H-dibenz[b,f]azepines or derivatives thereof, wherein the method is readily amenable to industrial batch-size production.

Moreover, the process of the present invention has been devised in such a manner that it can provide high yields of optically pure (S)-(+)- or (R)-(−)-10-hydroxy-dihydrodibenz [b,f]azepines or derivatives thereof without generation of the undesired isomer as in case of diastereomeric resolution processes, which can provide maximum yield of up to 50% with respect to desired isomer.

In an embodiment, the invention provides a process for preparing (S)-(+)-10,11-dihydro-10-hydroxy-5H-dibenz[b, f]azepines or (R)-(−)-10,11-dihydro-10-hydroxy-5H-dibenz [b,f]azepines or derivatives thereof, by enantioselective reduction of 10,11-dihydro-10-oxo-5H-dibenz[b,f]azepines or derivatives thereof in presence of boronate esters.

The process for enantioselective reduction of 10,11-dihydro-10-oxo-5H-dibenz[b,f]azepines or derivatives thereof in presence of boronate esters, wherein boronate ester is selected from dihydroxy compound derived esters of boronic acid or their derivatives.

In an another embodiment, the invention provides a process for preparing (S)-(+)-10,11-dihydro-10-hydroxy-5H-dibenz[b,f]azepines or (R)-(−)-10,11-dihydro-10-hydroxy-5H-dibenz[b,f]azepines, by enantioselective reduction of 10,11-dihydro-10-oxo-5H-dibenz[b,f]azepines or derivatives thereof in presence of borohydride compound and tartaric acid derived ester of boronic acid or there derivatives.

In an another embodiment, the invention provides a process for preparing (S)-(+)-10,11-dihydro-10-hydroxy-5H-dibenz[b,f]azepine-5-carboxamide or (R)-(−)-10,11-dihydro-10-hydroxy-5H-dibenz[b,f]azepine-5-carboxamide, by enantioselective reduction of 10,11-dihydro-10-oxo-5H-dibenz[b,f]azepine-5-carboxamide or derivatives thereof in presence of borohydride compound and tartaric acid derived ester of boronic acid or derivatives thereof.

In an another embodiment, the invention provides a process for preparing (S)-(+)-10,11-dihydro-10-hydroxy-5H-dibenz[b,f]azepine-5-carboxamide or (R)-(−)-10,11-dihydro-10-hydroxy-5H-dibenz[b,f]azepine-5-carboxamide, by enantioselective reduction of 10,11-dihydro-10-oxo-5H-dibenz[b,f]azepine-5-carboxamide or derivatives thereof in presence of borohydride compound and tartaric acid derived ester of phenyl boronic acid.

In an another embodiment, the invention provides a process for preparing (S)-(+)-10,11-dihydro-10-hydroxy-5H-dibenz[b,f]azepine-5-carboxamide or (R)-(−)-10,11-dihydro-10-hydroxy-5H-dibenz[b,f]azepine-5-carboxamide, by enantioselective reduction of 10,11-dihydro-10-oxo-5H-dibenz[b,f]azepine-5-carboxamide or derivatives thereof in presence of sodium borohydride and tartaric acid derived ester of phenyl boronic acid.

In an another embodiment, the invention provides a process for preparing (S)-(−)-10-acetoxy-10,11-dihydro-5H-dibenz[b,f]azepine-5-carboxamide, or (R)-(+)-10-acetoxy-10,11-dihydro-5H-dibenz[b,f]azepine-5-carboxamide from (S)-(+)-10,11-dihydro-10-hydroxy-5H-dibenz[b,f]azepine or (R)-(−)-10,11-dihydro-10-hydroxy-5H-dibenz[b,f] azepine, which are obtained by enantioselective reduction of 10,11-dihydro-10-oxo-5H-dibenz[b,f]azepine or derivatives thereof in presence of boronate esters.

In an another embodiment, the invention provides a process for preparing (S)-(−)-10-acetoxy-10,11-dihydro-5H-dibenz[b,f]azepine-5-carboxamide, or (R)-(+)-10-acetoxy-10,11-dihydro-5H-dibenz[b,f]azepine-5-carboxamide from (S)-(+)-10,11-dihydro-10-hydroxy-5H-dibenz[b,f]azepine or (R)-(−)-10,11-dihydro-10-hydroxy-5H-dibenz[b,f] azepine, which are obtained by enantioselective reduction of 10,11-dihydro-10-oxo-5H-dibenz[b,f]azepine or derivatives thereof in presence of borohydride compound and tartaric acid derived ester of phenyl boronic acid.

In an another embodiment, the invention provides a process for preparing (S)-(−)-10-acetoxy-10,11-dihydro-5H-dibenz[b,f]azepine-5-carboxamide, or (R)-(+)-10-acetoxy-10,11-dihydro-5H-dibenz[b,f]azepine-5-carboxamide from (S)-(+)-10,11-dihydro-10-hydroxy-5H-dibenz[b,f]azepine-5-carboxamide or (R)-(−)-10,11-dihydro-10-hydroxy-5H-dibenz[b,f]azepine-5-carboxamide, which are obtained by enantioselective reduction of 10,11-dihydro-10-oxo-5H-dibenz[b,f]azepine-5-carboxamide or derivatives thereof in presence of boronate esters.

In an another embodiment, the invention provides a process for preparing (S)-(−)-10-acetoxy-10,11-dihydro-5H-dibenz[b,f]azepine-5-carboxamide, or (R)-(+)-10-acetoxy-10,11-dihydro-5H-dibenz[b,f]azepine-5-carboxamide from (S)-(+)-10,11-dihydro-10-hydroxy-5H-dibenz[b,f]azepine-5-carboxamide or (R)-(−)-10,11-dihydro-10-hydroxy-5H-dibenz[b,f]azepine-5-carboxamide, which are obtained by enantioselective reduction of 10,11-dihydro-10-oxo-5H- dibenz[b,f]azepine-5-carboxamide or derivatives thereof in presence of sodium borohydride and tartaric acid derived ester of phenyl boronic acid.

In yet another embodiment, the invention provides a process for the preparation of optically pure (S)-(+)- or (R)-(−)-10,11-dihydro-10-hydroxy-5H-dibenz[b,f]azepine-5-carboxamide, comprising:

a) reacting 10,11-dihydro-10-oxo-5H-dibenz[b,f]azepine-5-carboxamide with boronate esters or their derivatives in presence of borohydride compounds to obtain (S)-(+)- or (R)-(−)-10,11-dihydro-10-hydroxy-5H-dibenz[b,f]azepine-5-carboxamide;

b) optionally, if $R_1$ is not —$CONH_2$ group then converting $R_1$ to —$CONH_2$ to obtain the optically pure (S)-(+)- or (R)-(−)-10,11-dihydro-10-hydroxy-5H-dibenz[b,f]azepine-5-carboxamide;

c) optionally, converting compound obtained after steps 'a' or 'b' into their prodrug esters of formula (I) or (Ia);

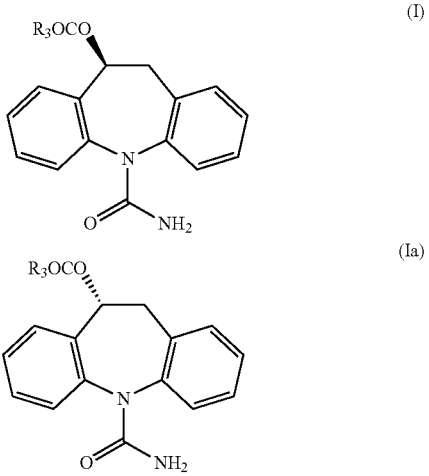

The invention, specifically with respect to (S)-(+)-10,11-dihydro-10-hydroxy-5H-dibenz[b,f]azepine-5-carboxamide and the other reagents, though not limited, can be read in concurrence with the reaction scheme as shown in Scheme II.

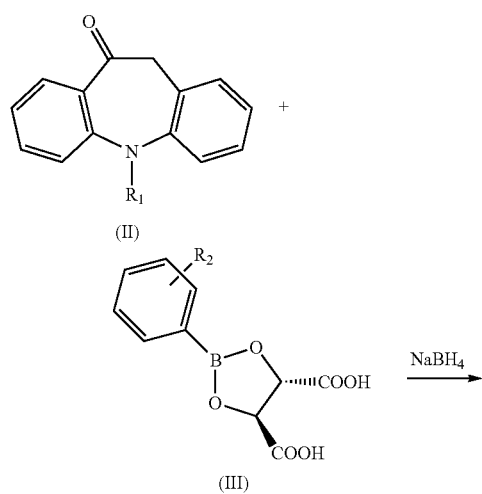

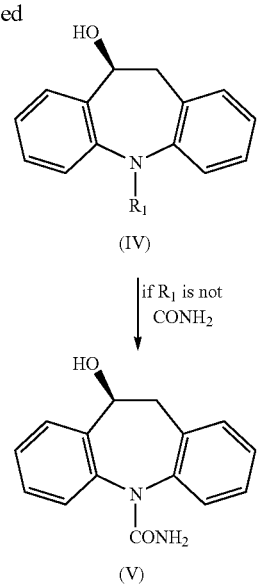

Wherein, $R_1$ is CN, —$CONH_2$, —CONHP (P is protecting group), —$COX_1$ ($X_1$ is halogen) or —$COOR_4$ $R_2$ may be but not restricted to hydrogen, alkyl, aryl, halogen, alkoxy, aryloxy, nitro, cyano, acyl, acyloxy and the like. The said substitution may further be substituted.

$R_3$ is alkyl, halogenalkyl, aralkyl, cycloalkyl, cycloalkylalkyl, alkoxy, aryl or pyridyl; the term alkyl means carbon chain, straight or branched, containing from 1 to 18 carbon atoms; the term halogen represents fluorine, chlorine, bromine or iodine; the term cycloalkyl represents an alicyclic saturated group with 3 to 6 carbon atoms; and the term aryl represents unsubstituted phenyl group or phenyl substituted by alkoxy, halogen, nitro and the like.

$R_4$ is acid protecting group such as alkyl, substituted or unsubstituted aryl or aralkyl group;

The substituted or unsubstituted boronate esters used in step 'a' can be obtained by reacting boronic acid derivatives, such as phenyl boronic acid or derivatives thereof, with a dihydroxy compound such as tartaric acid or derivatives thereof.

Borohydride compounds used in step 'a' can be selected from but not restricted to alkali metal borohydrides such as sodium borohydride, lithium borohydride, potassium borohydride, sodium cyanoborohydride, $NaBH(OAc)_3$ and the like; alkaline earth metal borohydrides such as magnesium borohydride, calcium borohydride and the like; transition metal borohydrides such as zinc borohydride and the like; tetra alkyl ammonium borohydrides such as tetra butyl ammonium borohydride and the like; lithium aluminum hydride, and the like; $BH_3$-ligand complex such as $BH_3$-THF complex and the like.

The reaction in the step 'a' for the preparation of (S)-(+)-10,11-dihydro-10-hydroxy-5H-dibenz[b,f]azepines or (R)-(−)-10,11-dihydro-10-hydroxy-5H-dibenz[b,f]azepines is carried out by enantioselective reduction of 10,11-dihydro-10-oxo-5H-dibenz[b,f]azepines in presence of solvent selected from the group comprising of ethers such as tetrahydrofuran, diethyl ether, dioxane, diglyme, tetraglyme and the like; amides such as N-methylpyrrolidine and the like; nitriles such as acetonitrile and the like; sulfoxides, hydrocarbons (aliphatic or aromatic) such as benzene, toluene and the like;

chlorinated hydrocarbons (aliphatic or aromatic) such as dichloromethane and the like or mixture thereof.

In another embodiment there is provided a pharmaceutical composition that includes therapeutically effective amount of (S)-(+)-10,11-dihydro-10-hydroxy-5H-dibenz[b,f]azepines or (R)-(−)-10,11-dihydro-10-hydroxy-5H-dibenz[b,f]azepines prepared by the process of present invention and one or more pharmaceutically acceptable carriers, excipients or diluents.

In yet another embodiment there is provided use of a pharmaceutical composition that includes a therapeutically effective amount (S)-(+)-10,11-dihydro-10-hydroxy-5H-dibenz[b,f]azepines or (R)-(−)-10,11-dihydro-10-hydroxy-5H-dibenz[b,f]azepines prepared by the process of present invention and one or more pharmaceutically acceptable carriers, excipients or diluents to treat conditions in a subject, in need thereof such as for the treatment of psychosomatic disturbances, epilepsy, trigeminal neuralgia, cerebral spasticity, affective brain disorder or nervous function alteration in degenerative and post-ischemic disease, bipolar disorder etc.

In another embodiment there is provided pharmaceutical composition that includes therapeutically effective amount of (S)-(−)-10-acetoxy-10,11-dihydro-5H-dibenz[b,f]azepine-5-carboxamide, or (R)-(+)-10-acetoxy-10,11-dihydro-5H-dibenz[b,f]azepine-5-carboxamide prepared by the process of present invention and one or more pharmaceutically acceptable carriers, excipients or diluents.

In yet another embodiment there is provided use of pharmaceutical composition that includes therapeutically effective amount (S)-(−)-10-acetoxy-10,11-dihydro-5H-dibenz[b,f]azepine-5-carboxamide, or (R)-(+)-10-acetoxy-10,11-dihydro-5H-dibenz[b,f]azepine-5-carboxamide prepared by the process of present invention and one or more pharmaceutically acceptable carriers, excipients or diluents to treat conditions in a subject, in need thereof such as for the treatment of psychosomatic disturbances, epilepsy, trigeminal neuralgia, cerebral spasticity, affective brain disorder or nervous function alteration in degenerative and post-ischemic disease, bipolar disorder etc.

In yet another embodiment the present invention provides novel solid state forms of eslicarbazepine i.e. crystalline and amorphous forms of eslicarbazepine.

In yet another embodiment the present invention provides a process for the preparation of the novel solid state forms i.e. crystalline and amorphous forms of eslicarbazepine. The said process comprises of dissolving eslicarbazepine in one or more solvents; and recovering the eslicarbazepine in the various solid state forms by the removal of solvent.

A "solvent" as defined herein is selected from the group comprising of alcohols, nitriles, ketones, esters, ethers, amides, dialkylsulfoxide, water or the mixtures thereof. Alcohols are selected from the group comprising of methanol, ethanol, n-propanol, isopropanol, n-butanol and the like. The nitriles are selected from the group comprising of acetonitrile, propionitrile, butyronitrile, valeronitrile and the like. Ketones are selected from the group comprising of acetone, methyl ethyl ketone, methyl isobutyl ketone etc. Esters are selected from the group comprising of ethyl acetate, propyl acetate and the like. Chlorinated solvents are selected from the group comprising of dichloromethane, chloroform, dichloroethane, chlorobenzene and the like. Ethers can be selected from the group comprising of diethyl ether, diisopropyl ether, tetrahydrofuran, dioxane and the like. Amides can be selected from the group comprising of dimethylformamide, dimethylacetamide, N-methyl formamide, N-methylpyrrolidine and the like. Dialkyl sulfoxide can be selected from the group comprising of dimethyl sulfoxide, sulfolane diethyl sulfoxide, dibutyl sulfoxide and the like.

A "water soluble organic solvent" as defined herein includes but not only limited to the solvents selected from the group comprising of alcohols such as methanol, ethanol and isopropanol and the like; ketones such as acetone methyl ethyl ketone and the like, lower alkyl glycol ethers such as methyl glycol and the like; dipolar aprotic solvents such as N,N-dimethyl formamide (DMF), N,N-dimethylacetamide (DMA), N-methyl pyrrolidine and dimethyl sulfoxide (DMSO), sulfolane and cyclic ethers such as tetrahydrofuran, dioxane and the like or mixture(s) thereof.

The invention provides the novel stable crystalline and amorphous forms of eslicarbazepine.

In yet another embodiment, the invention provides novel crystalline polymorphic form $J_1$ of eslicarbazepine.

The novel crystalline Form $J_1$ of eslicarbazepine is characterized by its X-ray powder diffraction ("XRPD") pattern substantially in accordance with the pattern as depicted in FIG. I.

The novel crystalline Form $J_1$ of eslicarbazepine is characterized by its infra red (IR) spectrum substantially as depicted in FIG. II.

The novel crystalline Form $J_1$ of eslicarbazepine is characterized by its Differential Scanning calorimetry (DSC) thermogram as depicted in FIG. III.

The novel crystalline Form $J_1$ of eslicarbazepine is characterized by graphic results of thermogravimetric analysis (TGA) as depicted in FIG. IV.

In an another embodiment the invention provides a process for the preparation of Form $J_1$ of eslicarbazepine which can be obtained by removing organic solvent(s) from a solution of water and organic solvent(s) in presence of excess of water.

In yet another embodiment, the invention provides the use of Form $J_1$ of eslicarbazepine to prepare the derivatives of eslicarbazepine, such as eslicarbazepine acetate.

In another aspect, there is provided a pharmaceutical composition that includes a therapeutically effective amount of novel crystalline Form $J_1$ of eslicarbazepine and one or more pharmaceutically acceptable carriers, excipients or diluents.

In yet another aspect there is provided a use of a pharmaceutical composition that includes a therapeutically effective amount of novel crystalline Form $J_1$ of eslicarbazepine and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In another embodiment, the invention provides novel crystalline polymorphic form $J_2$ of eslicarbazepine.

The novel crystalline Form $J_2$ of eslicarbazepine is characterized by its X-ray powder diffraction ("XRPD") pattern substantially in accordance with the pattern as depicted in FIG. V.

The novel crystalline Form $J_2$ of eslicarbazepine is characterized by its IR spectrum substantially as depicted in FIG. VI.

The novel crystalline Form $J_2$ of eslicarbazepine is characterized by its Differential Scanning calorimetry (DSC) thermogram as depicted in FIG. VII.

The novel crystalline Form $J_2$ of eslicarbazepine is characterized by graphic results of thermogravimetric analysis (TGA) as depicted in FIG. VIII.

In an another embodiment, the invention provides a process for the preparation of Form $J_2$ of eslicarbazepine, which can be obtained by removing organic solvent(s) from a solution of eslicarbazepine in organic solvent(s) followed by treatment with water or mixture thereof with organic solvent(s).

In yet another embodiment, the invention provides the use of Form $J_2$ of eslicarbazepine to prepare the derivatives of eslicarbazepine, such as eslicarbazepine acetate.

In another aspect, there is provided a pharmaceutical composition that includes a therapeutically effective amount of novel crystalline Form $J_2$ of eslicarbazepine and one or more pharmaceutically acceptable carriers, excipients or diluents.

In yet another aspect, there is provided a use of a pharmaceutical composition that includes a therapeutically effective amount of novel crystalline Form $J_2$ of eslicarbazepine and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In yet another embodiment, the invention provides novel crystalline polymorphic Form $J_3$ of eslicarbazepine.

The novel crystalline Form $J_3$ of eslicarbazepine is characterized by its X-ray powder diffraction ("XRPD") pattern substantially in accordance with the pattern as depicted in FIG. IX.

The novel crystalline Form $J_3$ of eslicarbazepine is characterized by its infra red (IR) spectrum substantially as depicted in FIG. X.

The novel crystalline Form $J_3$ of eslicarbazepine is characterized by its Differential Scanning calorimetry (DSC) thermogram as depicted in FIG. XI.

The novel crystalline Form $J_3$ of eslicarbazepine is characterized by graphic results of thermogravimetric analysis (TGA) as depicted in FIG. XII.

In another embodiment, the invention provides a process for the preparation of Form $J_3$ of eslicarbazepine, which can be obtained from a solution of eslicarbazepine in a mixture of water soluble organic solvent and water.

In yet another embodiment, the invention provides the use of Form $J_3$ of eslicarbazepine to prepare the derivatives of eslicarbazepine, such as eslicarbazepine acetate.

In another aspect, there is provided a pharmaceutical composition that includes a therapeutically effective amount of novel crystalline Form $J_3$ of eslicarbazepine and one or more pharmaceutically acceptable carriers, excipients or diluents.

In yet another aspect, there is provided a use of a pharmaceutical composition that includes a therapeutically effective amount of novel crystalline Form $J_3$ of eslicarbazepine and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In yet another embodiment, the invention provides novel crystalline polymorphic form $J_4$ of eslicarbazepine.

The novel crystalline Form $J_4$ of eslicarbazepine is characterized by its X-ray powder diffraction ("XRPD") pattern substantially in accordance with the pattern as depicted in FIG. XIII.

The novel crystalline Form $J_4$ of eslicarbazepine is characterized by its IR spectrum substantially as depicted in FIG. XIV.

The novel crystalline Form $J_4$ of eslicarbazepine is characterized by its Differential Scanning calorimetry (DSC) thermogram as depicted in FIG. XV.

The novel crystalline Form $J_4$ of eslicarbazepine is characterized by graphic results of thermogravimetric analysis (TGA) as depicted in FIG. XVI.

In another embodiment, the invention provides a process for the preparation of Form $J_4$ of eslicarbazepine which can be obtained by removing water miscible organic solvent(s) from a solution of water and water miscible organic solvent(s) in presence of less amount of water.

In yet another embodiment, the invention provides the use of Form $J_4$ of eslicarbazepine to prepare the derivatives of eslicarbazepine, such as eslicarbazepine acetate.

In another aspect, there is provided a pharmaceutical composition that includes a therapeutically effective amount of novel crystalline Form $J_4$ of eslicarbazepine and one or more pharmaceutically acceptable carriers, excipients or diluents.

In yet another aspect, there is provided a use of a pharmaceutical composition that includes a therapeutically effective amount of novel crystalline Form $J_4$ of eslicarbazepine and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In another embodiment, the invention provides amorphous Form of eslicarbazepine.

The amorphous Form of eslicarbazepine is characterized by its X-ray powder diffraction ("XRPD") pattern substantially in accordance with the pattern as depicted in FIG. XVII.

The amorphous Form of eslicarbazepine is characterized by its IR spectrum substantially as depicted in FIG. XVIII.

The amorphous Form of eslicarbazepine is characterized by its Differential Scanning calorimetry (DSC) thermogram as depicted in FIG. XIX.

The amorphous Form of eslicarbazepine is characterized by graphic results of thermogravimetric analysis (TGA) as depicted in FIG. XX.

An embodiment of the present invention provides a process for the preparation of the amorphous form of eslicarbazepine. The process comprises of dissolving eslicarbazepine in one or more solvents; and recovering the eslicarbazepine in the amorphous form by the removal of solvent.

The method for removal the solvent can be selected to obtain the amorphous form of eslicarbazepine using the processes comprising of spray drying, distillation under vacuum, roller drying, freeze drying i.e. lyophilization, thin film drying and the like.

In another embodiment, the eslicarbazepine is milled by grinding action between two surfaces till the time amorphous eslicarbazepine is obtained. Such milling can be carried out by using a traditional technique of compounding using a pestle and mortar or by milling machines that essentially work on the same principle. Examples of such milling machines can be selected from the group comprising of ball mills, roller mills, jet mills, gyratory mills, and the like.

In other embodiment, the invention provides a method for preparation of physical forms of eslicarbazepine by quenching a melt of eslicarbazepine.

In yet another embodiment, the invention provides the use of amorphous form of eslicarbazepine to prepare the derivatives of eslicarbazepine, such as eslicarbazepine acetate.

In another aspect, there is provided a pharmaceutical composition that includes a therapeutically effective amount of amorphous Form of eslicarbazepine and one or more pharmaceutically acceptable carriers, excipients or diluents.

In yet another aspect, there is provided a use of a pharmaceutical composition that includes a therapeutically effective amount amorphous Form of eslicarbazepine and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In another embodiment, the invention provides a crystalline polymorphic Form of eslicarbazepine acetate.

The crystalline Form of eslicarbazepine acetate is characterized by its X-ray powder diffraction ("XRPD") pattern substantially in accordance with the pattern as depicted in FIG. XXI.

The crystalline Form of eslicarbazepine acetate is characterized by its IR spectrum substantially as depicted in FIG. XXII.

The crystalline Form of eslicarbazepine acetate is characterized by its Differential Scanning calorimetry (DSC) thermogram as depicted in FIG. XXIII.

The crystalline Form of eslicarbazepine acetate is characterized by graphic results of thermogravimetric analysis (TGA) as depicted in FIG. XXIV.

In an another embodiment, the invention provides a process for the preparation of crystalline Form of eslicarbazepine acetate, which can be obtained by crystallization using a solvent or mixture of solvents or by removal of solvent(s) from a solution of eslicarbazepine acetate or by precipitation of a solution of eslicarbazepine acetate in organic solvent(s) using anti-solvent.

In another aspect, there is provided a pharmaceutical composition that includes a therapeutically effective amount of crystalline Form of eslicarbazepine acetate and one or more pharmaceutically acceptable carriers, excipients or diluents.

In yet another aspect, there is provided a use of a pharmaceutical composition that includes a therapeutically effective amount crystalline Form of eslicarbazepine acetate and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In another embodiment, the invention provides amorphous Form of eslicarbazepine acetate.

The amorphous Form of eslicarbazepine acetate is characterized by its X-ray powder diffraction ("XRPD") pattern substantially in accordance with the pattern as depicted in FIG. XXV.

The amorphous Form of eslicarbazepine acetate is characterized by its IR spectrum substantially as depicted in FIG. XXVI.

The amorphous Form of eslicarbazepine acetate is characterized by its Differential Scanning calorimetry (DSC) thermogram as depicted in FIG. XXVII.

The amorphous Form of eslicarbazepine acetate is characterized by graphic results of thermogravimetric analysis (TGA) as depicted in FIG. XXVIII.

An embodiment of the present invention provides a process for the preparation of the amorphous form of eslicarbazepine acetate. The process comprises of dissolving eslicarbazepine acetate in one or more solvents; and recovering the eslicarbazepine acetate in the amorphous form by the removal of solvent.

The method for removal of the solvent to obtain the amorphous form of eslicarbazepine acetate can be selected from the processes comprising of spray drying, distillation under vacuum, roller drying, freeze drying i.e. lyophilization, thin film drying and the like.

In another embodiment, the eslicarbazepine acetate is milled by grinding action between two surfaces till the time amorphous eslicarbazepine acetate is obtained. Such milling can be carried out by using a traditional technique of compounding using a pestle and mortar or by milling machines that essentially work on the same principle. Examples of such milling machines can be selected from the group comprising of ball mills, roller mills, jet mills, gyratory mills, and the like.

In other embodiment, the invention provides a method for preparation of physical forms of eslicarbazepine acetate by quenching a melt of eslicarbazepine acetate.

In yet another embodiment, the invention provides the use of amorphous form of eslicarbazepine acetate to prepare other polymorphic forms of eslicarbazepine acetate.

In another aspect, there is provided a pharmaceutical composition that includes a therapeutically effective amount of amorphous form of eslicarbazepine acetate as depicted above and one or more pharmaceutically acceptable carriers, excipients or diluents.

In yet another aspect there is provided a use of a pharmaceutical composition that includes a therapeutically effective amount amorphous form of eslicarbazepine acetate as depicted above and one or more pharmaceutically acceptable carriers, excipients or diluents to treat conditions in a subject, in need thereof such as for the treatment psychosomatic disturbances, epilepsy, trigeminal neuralgia, cerebral spasticity, affective brain disorder or nervous function alteration in degenerative and post-ischemic disease, bipolar disorder etc.

In yet another aspect of the invention, the eslicarbazepine has particles size having $d_{0.9}$ less than 200 µm, $d_{0.5}$ less than 80 µm and $d_{0.1}$ less than 35 µm.

In yet another aspect of the invention, the eslicarbazepine acetate has particles size having $d_{0.9}$ less than 200 µm, $d_{0.5}$ less than 70 µm and $d_{01}$ less than 20 µm.

The process for the preparation of (S)-(+)- and (R)-(−)-10,11-dihydro-10-hydroxy-5H-dibenz[b,f]azepine-5-carboxamide derivatives described in the present invention is demonstrated in the examples illustrated below. These examples are provided as illustration only and therefore should not be constructed as limitation of the scope of the invention.

EXAMPLES

Example 1

Preparation of Eslicarbazepine

A solution of phenyl boronic acid (48.5 gm), D-(−)-tartaric acid (59.4 gm), calcium hydride (33.2 gm) in acetonitrile (750 mL) was heated to about 80-85° C. for about 1 hr. The reaction mass was cooled to about 25-30° C. ('Solution X'). A solution of oxcarbazepine (50 gm) in acetonitrile (250 mL) was prepared separately. 'Solution X' obtained above was added to the solution of oxcarbazepine followed by stirring the reaction mass for about 2 hrs. To the resulting solution sodium borohydride (59.4 gm) was added at about 30-35° C. The reaction mass was stirred at the same temperature for about 8-10 hrs followed by distillation of solvent. To the resulting residue water (1000 mL) was added. The pH of the resulting solution was adjusted to about 12-13 by adding NaOH solution. The reaction mass was heated to about 55-60° C. followed by stirring at the same temperature for about 1 hr. consequently, cooled the reaction mass to about 20-25° C. The reaction mass was stirred at the same temperature for about 4 hrs. The reaction mass was again cooled to about 10-15° C. and stirred for about 3 hrs. The resulting solid (35 gm) was filtered, washed and dried to obtain the title compound (Yield: 70%; HPLC purity: 99.5%; Chiral purity: 96.4%; $d_{0.9}$ 114.3 µm, $d_{0.5}$ 53.1 µm, $d_{0.1}$ 22 µm).

Example 2

Preparation of Eslicarbazepine

A solution of phenyl boronic acid (19.4 gm), D-(−)-tartaric acid (23.8 gm), calcium hydride (13.3 gm) in acetonitrile (300 mL) was heated to about 80-85° C. for about 1 hr. The reaction mass was cooled to 25-30° C. ('Solution X'). A solution of oxcarbazepine (20 gm) in acetonitrile (100 mL) was prepared separately. 'Solution X' obtained above was added to the solution of oxcarbazepine followed by stirring the reaction mass for about 2 hrs. To the resulting solution sodium borohydride (4.5 gm) was added at about 30-35° C. The reaction mass was stirred at the same temperature for about 8 hrs. The pH of the resulting solution was adjusted to 1-2 by adding HCl (3N, 200 mL) followed by stirring for about 30 minutes. To the resulting solution, NaOH (20% w/v) solution was added to adjust the pH at about 12-13. Dichloromethane was added to the resulting solution followed by stirring. The organic layer was separated and distilled to obtain the title compound (Yield: 91%; HPLC purity: 98.6%; Chiral purity: 92.5%).

Example 3

Preparation of Eslicarbazepine Acetate

A solution of eslicarbazepine (18 gm), triethylamine (8.5 gm), dimethylaminopyridine (0.1 gm), acetic anhydride (8.7 gm) and dichloromethane (90 mL) was stirred at about 20-25° C. for about 4 hrs. To the resulting solution water was added and resulting solution was stirred for about 15 minutes. Organic layer was separated and washed with 1 N HCl solution followed by washing with water. The solvent was distilled out completely. Ethyl acetate was added to the resulting residue followed by stirring at about 25-30° C. for about 3 hrs. The resulting solid was filtered, washed and dried to obtain the title compound (Yield: 80%; HPLC purity: 99.8%; Chiral purity: 99.3%; $d_{0.9}$ 50.7 µm, $d_{0.5}$ 17.3 µm, $d_{0.1}$ 6.0 µm).

Example 4

Preparation of Eslicarbazapine Acetate

To a solution of eslicarbazepine (30 gm), triethylamine (19.7 gm), dimethylaminopyridine (0.15 gm), and dichloromethane (150 mL), acetic anhydride (14.5 mL in 14.5 mL dichloromethane) was added and solution was stirred at about 20-25° C. for about 3 hrs. The resulting solution was cooled to about 10-15° C. To the resulting solution water (90 mL) was added followed by addition of HCl till pH of the resulting solution was 1-2. Organic layer was separated and washed with water. Water was added to organic layer followed by cooling to about 10-15° C. The pH of the resulting solution was adjusted to 9-10 by adding NaOH (10% w/v) solution. Organic layer was separated and solvent was distilled out completely to obtain the title compound.

Example 5

Purification of Eslicarbazepine Acetate

To a solution of eslicarbazepine acetate (22 gm) isopropanol (110 mL) was added and the reaction mass was heated to about 80-85° C. followed by stirring for about 1 hr. The reaction mass was cooled to about 30° C. followed by stirring at the same temperature for about 1 hr. The resulting solid was filtered, washed with isopropanol and dried to obtain the title compound. (The above purification step may be repeated one or more times to obtain the desired purity.) Yield: 79%; HPLC purity: 99.9%; Chiral purity: 99.9%; $d_{0.9}$ 90.3 µm, $d_{0.5}$ 44.2 µm, $d_{0.1}$ 10.7 µm).

Example 6

Preparation of N-Boc-phenylalanine

L-phenylalanine (50 gm) in water (50 mL) is stirred for about 30 minutes and reaction mass was cooled to 10-15° C. To the resulting solution aq. NaOH is added followed by addition of Boc anhydride (39.5 mL). Stirred the reaction mass at about 25° C. for about 4-5 h. Cyclohexane and water was added to the resulting solution followed by layer separation. The aq. layer was cooled and aq. $KHSO_4$ solution was charged to it with subsequent addition of ethyl acetate (250 mL). Ethyl acetate layer was separated and washed with water. Ethyl acetate was distilled off completely. Cyclohexane and ethyl acetate was added to the residue. Reaction mass was cooled to 5-10° C. and stirred for 4-5 h. The reaction mass filtered, washed with chilled cyclohexane and dried under vacuum to obtain the title compound.

Example 7

Preparation of 2-isobutoxycarbonylamino-3-phenyl-propionic acid

L-phenylalanine (50 gm) in water (50 mL) was stirred for about 30 minutes and reaction mass was cooled to 10-15° C. To the resulting solution, aq. NaOH was added followed by addition of isobutylchloroformate (45.5 gm). The reaction mass was stirred at about 25° C. for about 3-4 h and pH was adjusted to 2-3 by addition of conc. HCl at 10-15° C. Reaction mass was stirred at 10-15° C. for 1 h, filtered, washed with water and dried to obtain the title compound.

Example 8

Preparation of (1-chlorocarbonyl-2-phenylethan-1-yl)-carbamic acid isobutyl ester A solution of 2-isobutoxycarbonylamino-3-phenyl-propionic acid (5 gm), dichloromethane (25 mL) and dimethylformamide (0.5 mL) was cooled to 0-5° C. To the resulting solution, thionyl chloride (1.5 mL) was added at same temperature. The solvent was distilled out completely to obtain the title compound.

Example 9

Preparation of Isobutyloxycarbonyl Protected Phenylalanine Ester of Licarbazapine A solution of (1-chlorocarbonyl-2-phenyl-ethyl)-carbamic acid isobutyl ester (5 gm), obtained solution in dichloromethane was added to a solution of licarbazepine (4 gm), pyridine (2.2 mL), dimethylaminopyridine (0.05 gm) and dichloromethane (60 mL) at 5-10° C. Reaction mass was stirred at room temperature for 4 h and washed with water. The solvent was distilled to obtain the title compound.

Example 10

Preparation of Isobutyloxycarbonyl Protected Phenylalanine Ester of Eslicarbazapine A solution of isobutyl carbamate protected phenylalanine ester of licarbazapine (5 gm) in methanol (1.5 mL) and ethyl acetate (50 mL) was heated to 70-75° C. The reaction mass was cooled to about 30° C. and stirred for about 1 h at the same temperature. Reaction mass was filtered, washed with ethyl acetate and dried to obtain the title compound.

Example 11

Preparation of N-Boc-Protected Phenylalanine Ester of Licarbazapine

A solution of N-Boc phenylalnine (15 gm) and triethyl amine (11.9 gm) in dichloromethane (60 mL) was cooled to 0-5° C. To the resulting solution pivaloyl chloride (6.5 mL) was added at same temperature. The reaction mass was stirred for 1 h at 20-25° C. and then filtered. Thus obtained filtrate was added to a solution of licarbazepine, pyridine (5.5 g), dimethylaminopyridine (1 gm) in dichloromethane (60 mL) at 20-25° C. Reaction mass was stirred for 3-4 h and washed with 2% sodium bicarbonate solution (50 mL). The solvent was distilled to obtain the title compound.

Example 12

Preparation of N-Boc-Protected Phenylalanine Ester of Licarbazapine

A solution of licarbazepine (4 g), dimethylaminopyridine (0.05 gm), N-Boc. phenylalanine (2.2 mL) and dichloromethane (60 mL) was cooled to 5-10° C. N,N-dicyclohexylcarbodiimide (DCC) was added to the above solution followed by stirring at 5-10° C. for about 6 h. The temperature was raised to 25-30° C. and reaction mass was filtered and washed with chilled dichloromethane (12 mL). The filtrate was distilled to obtain the title compound.

Example 13a

Preparation of N-Boc-Protected Phenylalanine Ester of Eslicarbazapine

A solution of N-Boc protected phenylalanine ester of licarbazapine (33 gm) in dichloromethane (200 mL) was heated to 35-40° C. The reaction mass was cooled to 0° C. and stirred for about 1 h at the same temperature. Reaction mass was filtered, washed with chilled dichloromethane and dried to obtain the title compound.

Example 13b

Preparation of N-Boc-Protected Phenylalanine Ester of Eslicarbazapine

A solution of N-Boc protected phenylalanine ester of licarbazapine (5 gm) in methanol (100 mL) and water (10 mL) was heated to 65-70° C. The reaction mass was cooled to 30° C. Stirred the reaction mass at 65-70° C. for 1 h. Reaction mass was filtered, washed with methanol and dried to obtain the title compound.

Example 14

Preparation of Eslicarbazepine (Form $J_1$) from N-isobutyl Carbamate Ester

To a solution of isobutyl carbamate protected phenylalanine ester of eslicarbazepine (15 gm) in methanol (45 mL), was added aq. solution of NaOH (1.8 gm NaOH in 120 mL) 25-30° C. The mixture was stirred at 25-30° C. for 3 hrs. To the resulting mixture dichloromethane (45 mL) was added and stirred for 1 hr. The reaction mass was distilled out under vacuum at 50-55° C. Then 7 mL methanol and 80 mL water was added to the residue followed by heating at 75-80° C. for 30 min. The reaction mass was cooled to 25-30° C. and stirred for 2 hrs. Solid was filtered and dried under vacuum at 50-55° C. to obtain the title compound (m. p. 188.5-190.5° C.).

Example 15

Preparation of Eslicarbazepine (Form $J_2$) from N-Isobutyl Carbamate Ester

To a solution of isobutyl carbamate protected phenylalanine ester of eslicarbazepine (27 gm) in dichloromethane (216 mL), aq. solution of NaOH (3.25 gm NaOH in 162 mL water) was added at 25-30° C. Stirred the reaction mass at 25-30° C. for 2 hrs followed by stirring at 35-40° C. for 2 hrs. Added 270 mL methanol and stirred at 25-30° C. for 2 hrs. Dichloromethane (135 mL) was added and stirred. Organic layer was collected. Aq. layer was concentrated under vacuum at 50-55° C. and then cooled to room temperature. Extracted the aq. layer with dichloromethane (2×200 mL) and combined organic layer was distilled under vacuum at 50-55° C. Then 27 ml water was added to the residue and heated at 65-70° C. The reaction mixture was cooled and stirred at 25-30° C. for 2 hrs. Solid was filtered, washed with water and dried under vacuum at 50-55° C. to obtain the title compound (m. p. 189.3-190.1° C.).

Example 16

Preparation of Polymorphic Form $J_3$ of Eslicarbazepine

A solution of eslicarbazepine (500 mg) in methanol (7 mL) was heated at 40-45° C. for 15 min. The reaction mass was cooled at 25-30° C. The solution was filtered. The solution was concentrated and followed by addition of 20 mL of water. Cooled the clear solution to 5-10° C. and stirred for 30 min. Filtered the solid, washed with water and dried to obtain title compound (m. p. 186.1-190.1° C.).

Example 17

Preparation of Polymorphic Form $J_3$ of Eslicarbazepine

A solution of eslicarbazepine (500 mg) in methanol (10 mL) was stirred at 25-30° C. for 15 min. Added 20 mL water to the solution. Distilled out solvent under vacuum at 50-55° C. slowly, till the precipitation starts. Stirred the suspended solution at 25-30° C. for 30 min. Solution is filtered, washed and dried to obtain title compound (m. p. 186.1-190.1° C.).

Example 18

Preparation of Form J₄ of Eslicarbazapine

To a solution of N-Boc protected phenylalanine ester of eslicarbazapine (45 gm) in methanol (270 mL), aq. NaOH (3N, 126 mL) was added at 20-25° C. Stirred the reaction mass at 25-30° C. for 1 h and distilled out solvent completely under vacuum at 50-55° C. Water was added to the residue followed by heating at 65-70° C. for 1 h, then cooled to 25-30° C., and stirred for 3 hrs at 25-30° C. further cooled to 5-10° C. and stirred for 1 hr at 5-10° C. Reaction mass was filtered, washed and dried to obtain the title compound (m. p. 183.8-185.8° C.).

Example 19

Preparation of Amorphous Eslicarbazepine

A solution of eslicarbazepine (500 mg) in methanol (10 mL) was heated at 40-45° C. for 15 min. Cooled the solution at 30° C. The solution was filtered and the solvent was distilled out. The solid residue was dried to obtain the title compound (m. p. 70.4-100.9° C.).

Example 20

Preparation of Amorphous Eslicarbazepine

A suspension of eslicarbazepine (500 mg) in dichloromethane (18 mL) was heated at 35-40° C. for 1 hr. Added methanol (5 mL) to make solution clear and continue heating for another 15 min. Cooled the solution at 25-30° C. The solvent was distilled out under vacuum at 40° C. till complete dryness. Solid residue was dried under vacuum at 50° C. for 2 hrs.

Example 21

Preparation of Eslicarbazapine Acetate

A solution of eslicarbazepine (15.0 gm), pyridine (8 mL), dimethylaminopyridine (0.17 gm) in dichloromethane (150 mL) was cooled to 5-10° C. Added acetyl chloride (7.6 mL) at about 5-10° C. followed by stirring at 35-40° C. for about 5-6 h. Washed the reaction mass with 0.5N HCl solution (45 mL) and followed by washing the organic layer with water (100 mL). Distilled out the solvent completely under vacuum to obtain crude eslicarbazepine acetate. The residue was dissolved in a mixture (60 mL) of dichloromethane and ethyl acetate (1:1) at 35-40° C. then cooled to 25-30° C. Reaction mass was filtered, washed with ethyl acetate and dried to obtain the title compound (m. p. 186.0-187.2° C.).

Example 22

Preparation of Amorphous Eslicarbazepine Acetate

Eslicarbazepine Acetate (1 g) was dissolved in methylene dichloride (30 mL). The resulting solution was distilled in preheated water bath to obtain amorphous eslicarbazepine acetate (m. p. 184.6-185.4° C.).

The invention claimed is:

1. A process for preparing (S)-(+)-10,11-dihydro-10-hydroxy-5H-dibenz[b,f]azepines or (R)-(−)-10,11-dihydro-10-hydroxy-5H-dibenz[b,f]azepines or esters thereof, by enantioselective reduction of 10,11-dihydro-10-oxo-5H-dibenz[b,f]azepines or esters thereof in presence of boronate esters.

2. The process according to claim 1, wherein (S)-(+)-10,11-dihydro-10-hydroxy-5H-dibenz[b,f]azepines and (R)-(−)-10,11-dihydro-10-hydroxy-5H-dibenz[b,f]azepines are (S)-(+)-10,11-dihydro-10-hydroxy-5H-dibenz[b,f]azepine-5-carboxamide and (R)-(−)-10,11-dihydro-10-hydroxy-5H-dibenz[b,f]azepine-5-carboxamide respectively.

3. The process according to claim 1, wherein (S)-(+)-10,11-dihydro-10-hydroxy-5H-dibenz[b,f]azepines, is (S)-(+)-10,11-dihydro-10-hydroxy-5H-dibenz[b,f]azepine-5-carboxamide.

4. The process according to claim 1, further comprising preparing (S)-(−)-10-acetoxy-10,11-dihydro-5H-dibenz[b,f]azepine-5-azepine, or (R)-(+)-10-acetoxy-10,11-dihydro-5H-dibenz[b,f]azepine-5-azepine from (S)-(+)-10,11-dihydro-10-hydroxy-5H-dibenz[b,f]azepine or (R)-(−)-10,11-dihydro-10-hydroxy-5H-dibenz[b,f]azepine, which are obtained by enantioselective reduction of 10,11-dihydro-10-oxo-5H-dibenz[b,f]azepine or esters thereof in presence of boronate esters.

5. The process according to claim 1, for the preparation of optically pure (S)-(+)-10,11-dihydro-10-hydroxy-5H-dibenz[b,f]azepine-5-carboxamide (V) or (R)-(−)-10,11-dihydro-10-hydroxy-5H-dibenz[b,f]azepine-5-carboxamide (Va) or esters thereof, comprising:

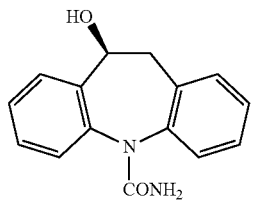

(V)

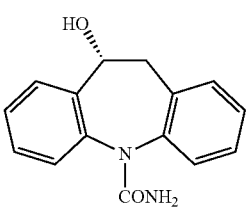

(Va)

a) reacting 10,11-dihydro-10-oxo-5H-dibenz[b,f]azepine-5-carboxamide (II) with boronate esters in presence of borohydride compounds to obtain (S)-(+)- or (R)-(−)-10,11-dihydro-10-hydroxy-5H-dibenz[b,f]azepine-5-carboxamide;

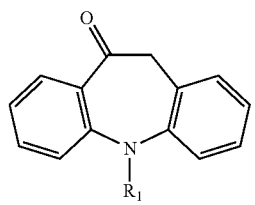

(II)

b) optionally, if $R_1$ is not —$CONH_2$ group then converting $R_1$ to —$CONH_2$ to obtain the optically pure (S)-(+)- or (R)-(−)-10,11-dihydro-10-hydroxy-5H-dibenz[b,f]azepine-5-carboxamide;

c) optionally, converting compound obtained after steps 'a' or 'b' into their esters of formula (I) or (Ia);

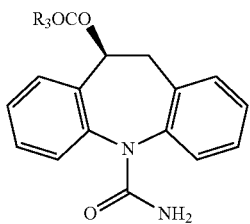
(I)

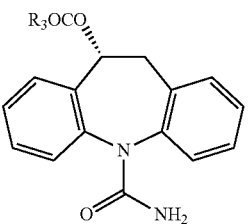
(Ia)

wherein, $R_1$ is CN, —$CONH_2$, —CONHP (P is protecting group), —$COX_1$ ($X_1$ is halogen) or —$COOR_4$;

$R_3$ is alkyl, halogenalkyl, aralkyl, cycloalkyl, cycloalkylalkyl, alkoxy, aryl or pyridyl; the term alkyl means carbon chain, straight or branched, containing from 1 to 18 carbon atoms; the term halogen represents fluorine, chlorine, bromine or iodine; the term cycloalkyl represents an alicyclic saturated group with 3 to 6 carbon atoms; and the term aryl represents unsubstituted phenyl group or phenyl substituted by alkoxy, halogen, nitro;

$R_4$ is acid protecting group selected from alkyl, substituted or unsubstituted aryl or aralkyl group.

6. The process according to claim 1, wherein (a) boronate ester is selected from dihydroxy compound derived esters of boronic acid; (b) enantioselective reduction with boronate ester is carried out in presence of a borohydride compound, wherein borohydride compound is selected from the group comprising of alkali metal borohydrides, alkaline earth metal borohydrides, transition metal borohydrides, tetra alkyl ammonium borohydrides, lithium aluminum hydrides and $BH_3$-ligand complex; alkali metal borohydride is selected from the group comprising of sodium borohydride, lithium borohydride, potassium borohydride, sodium cyanoborohydride and $NaBH(OAc)_3$ and alkaline earth metal borohydride is selected from the group comprising of magnesium borohydride and calcium borohydride.

7. The process according to claim 1, wherein boronate ester is selected from compound of formula III;

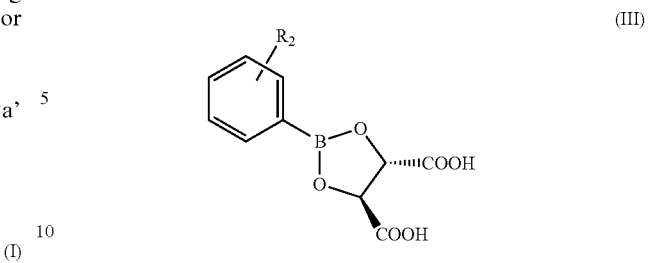
(III)

wherein $R_2$ is selected from the group comprising of hydrogen, alkyl, aryl, halogen, alkoxy, aryloxy, nitro, cyano, acyl and acyloxy.

8. A pharmaceutical composition comprising a therapeutically effective amount of compounds selected from (S)-(+)-10,11-dihydro-10-hydroxy-5H-dibenz[b,f]azepine-5-carboxamide, (R)-(−)-10,11-dihydro-10-hydroxy-5H-dibenz[b,f]azepine-5-carboxamide, (S)-(−)-10-acetoxy-10,11-dihydro-5H-dibenz[b,f]azepine-5-carboxamide, and (R)-(+)-10-acetoxy-10,11-dihydro-5H-dibenz[b,f]azepine-5-carboxamide prepared according to the process of claim 1, 2, 3, 4, 5, 6 or 7 and one or more pharmaceutically acceptable carriers, excipients or diluents.

9. A method of treating psychosomatic disturbances, epilepsy, trigeminal neuralgia, cerebral spasticity, affective brain disorder or nervous function alteration in degenerative and post-ischemic disease, bipolar disorder, by administering a pharmaceutical composition of claim 8.

10. (S)-(+)-10,11-dihydro-10-hydroxy-5H-dibenz[b,f]azepines according to claim 1, having particles size distribution as $d_{0.9}$ less than 200 μm, $d_{0.5}$ less than 80 μm and $d_{0.1}$ less than 35 μm or (S)-(+)-10,11-dihydro-10-hydroxy-5H-dibenz[b,f]azepines esters according to claim 1 having particles size distribution as $d_{0.9}$ less than 200 μm, $d_{0.5}$ less than 70 μm and $d_{0.1}$ less than 20 μm.

11. Polymorphic form $J_1$, $J_2$, $J_3$, $J_4$ or amorphous form of eslicarbazepine having the following characteristics wherein:

(a) crystalline polymorphic form $J_1$ of eslicarbazepine is characterized by at least one or more of following properties:

i) a X-ray powder diffraction ("XRPD") pattern substantially in accordance with the pattern as depicted in FIG. I;

ii) a differential Scanning calorimetry (DSC) thermogram as depicted in FIG. III and iii) a process for the preparation of Form $J_1$ of eslicarbazepine comprising removing organic solvent(s) from a solution of eslicarbazepine in water and organic solvent(s) in presence of excess of water or (b) crystalline polymorphic form $J_2$ of eslicarbazepine is characterized by at least one or more of following properties:

i) a X-ray powder diffraction ("XRPD") pattern substantially in accordance with the pattern as depicted in FIG. V;

ii) a differential Scanning calorimetry (DSC) thermogram as depicted in FIG. VII and iii) a process for the preparation of Form $J_2$ of eslicarbazepine, comprising removing organic solvent(s) from a solution of eslicarbazepine in organic solvent(s) followed by treatment with water or mixture thereof with organic solvent(s) or (c) crystalline polymorphic form $J_3$ of eslicarbazepine is characterized by at least one or more of following properties:

i) a X-ray powder diffraction ("XRPD") pattern substantially in accordance with the pattern as depicted in FIG. IX;
ii) a Differential Scanning calorimetry (DSC) thermogram as depicted in FIG. XI and
iii) a process for the preparation of Form $J_3$ of eslicarbazepine, comprising obtaining eslicarbazepine from a solution of eslicarbazepine in a mixture of water soluble organic solvent and water or (d) crystalline polymorphic form $J_4$ of eslicarbazepine is characterized by at least one or more of following properties:
i) a X-ray powder diffraction ("XRPD") pattern substantially in accordance with the pattern as depicted in FIG. XIII;
ii) a differential Scanning calorimetry (DSC) thermogram as depicted in FIG. XV and
iii) a process for the preparation of Form $J_4$ of eslicarbazepine comprising removing water miscible organic solvent(s) from a solution of eslicarbazepine in water and water miscible organic solvent(s) in presence of less amount of water or (e) amorphous eslicarbazepine which is prepared by the process which comprises of dissolving eslicarbazepine in one or more solvents; and recovering the eslicarbazepine in the amorphous form by the removal of solvent.

12. The process according to claim 1 wherein (S)-(+)-10,11-dihydro-10-hydroxy-5H-dibenz[b,f]azepines or (R)-(-)-10,11-dihydro-10-hydroxy-5H-dibenz[b,f]azepines is further converted to eslicarbazepine acetate, characterized by at least one of the following properties wherein:

(a) crystalline polymorphic form of eslicarbazepine acetate is characterized by at least one or more of following properties:
i) a X-ray powder diffraction ("XRPD") pattern substantially in accordance with the pattern as depicted in FIG. XXI
ii) a differential Scanning calorimetry (DSC) thermogram as depicted in FIG. XXIII and
iii) a process for the preparation of crystalline Form of eslicarbazepine acetate, comprising crystallization using a solvent or mixture of solvents or by removal of solvent(s) from a solution of eslicarbazepine acetate or by precipitation of a solution of eslicarbazepine acetate in organic solvent(s) using anti-solvent or (b) amorphous eslicarbazepine acetate which is prepared by the process which comprises of dissolving eslicarbazepine acetate in one or more solvents; and recovering the eslicarbazepine acetate in the amorphous form by the removal of solvent.

13. The polymorphic form $J_1$, $J_2$, $J_3$, $J_4$ or amorphous form of eslicarbazepine according to claim 11 wherein Form $J_1$, $J_2$, $J_3$, $J_4$ or amorphous form of eslicarbazepine is further converted to eslicarbazepine acetate.

14. The process according to claim 12, wherein method for removal of solvent is selected from the processes comprising of spray drying, distillation under vacuum, roller drying, freeze drying and thin film drying and the solvent is selected from the group comprising of alcohols, nitriles, ketones, esters, ethers, amides, dialkylsulfoxide, hydrocarbons (aliphatic or aromatic), chlorinated hydrocarbon, lower alkyl glycol ethers, dipolar aprotic solvent, sulpholane, cyclic ether, water or the mixtures thereof.

* * * * *